US009340715B2

(12) United States Patent
Matson et al.

(10) Patent No.: US 9,340,715 B2
(45) Date of Patent: *May 17, 2016

(54) METHODS OF MERCAPTANIZING OLEFINIC HYDROCARBONS AND COMPOSITIONS PRODUCED THEREFROM

(71) Applicant: Chevron Phillips Chemical Company LP, The Woodlands, TX (US)

(72) Inventors: Michael S. Matson, Bartlesville, OK (US); Colin Cameron, Stocksfield (GB); Alastair Robert Marrion, Morpeth (GB); Anthony Colin Wright, Gateshead (GB); Mitchell D. Refvik, Bartlesville, OK (US); Eric J. Netemeyer, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/820,610

(22) Filed: Aug. 7, 2015

(65) Prior Publication Data

US 2015/0344742 A1     Dec. 3, 2015

Related U.S. Application Data

(62) Division of application No. 13/891,224, filed on May 10, 2013, now Pat. No. 9,133,370, which is a division of application No. 12/849,072, filed on Aug. 3, 2010, now Pat. No. 8,461,293.

(51) Int. Cl.
| | |
|---|---|
| *C08J 11/06* | (2006.01) |
| *C09J 175/04* | (2006.01) |
| *C09J 201/00* | (2006.01) |
| *C09J 163/00* | (2006.01) |
| *C07C 319/04* | (2006.01) |
| *C07C 321/06* | (2006.01) |
| *C07C 321/10* | (2006.01) |
| *C07C 321/22* | (2006.01) |
| *C09J 11/06* | (2006.01) |
| *C08G 75/10* | (2006.01) |
| *C08G 75/14* | (2006.01) |
| *C08G 75/16* | (2006.01) |

(52) U.S. Cl.
CPC ............. *C09J 175/04* (2013.01); *C07C 319/04* (2013.01); *C07C 321/06* (2013.01); *C07C 321/10* (2013.01); *C07C 321/22* (2013.01); *C09J 11/06* (2013.01); *C09J 163/00* (2013.01); *C09J 201/00* (2013.01); *C07C 2101/14* (2013.01); *C07C 2101/18* (2013.01); *C07C 2101/20* (2013.01)

(58) Field of Classification Search
CPC ...................................................... C08J 11/06

USPC ............ 528/387, 373, 374, 375, 398; 522/76; 524/710

See application file for complete search history.

(56) References Cited

U.S. PATENT DOCUMENTS

| | | | |
|---|---|---|---|
| 3,081,352 A | 3/1963 | Gardner et al. | |
| 3,223,738 A | 12/1965 | Crain et al. | |
| 3,505,166 A | 4/1970 | Jones et al. | |
| 3,616,374 A | 10/1971 | Goshorn et al. | |
| 3,624,160 A | 11/1971 | Jones et al. | |
| 3,625,925 A | 12/1971 | Oswald et al. | |
| 3,940,374 A | 2/1976 | Oswald et al. | |
| 4,140,604 A | 2/1979 | Dimmig | |
| 4,612,398 A | 9/1986 | Lee | |
| 5,374,668 A | 12/1994 | Kanemura et al. | |
| 8,461,293 B2 | 6/2013 | Matson et al. | |
| 9,133,370 B2 * | 9/2015 | Matson .................... | C09J 11/06 528/387 |
| 2010/0010267 A1 | 1/2010 | Deck et al. | |
| 2014/0131618 A1 | 5/2014 | Matson | |
| 2015/0344752 A1 | 12/2015 | Matson et al. | |
| 2015/0344756 A1 | 12/2015 | Matson et al. | |

FOREIGN PATENT DOCUMENTS

| | | |
|---|---|---|
| EP | 0272181 | 6/1988 |
| GB | 1 283 832 | 8/1972 |

OTHER PUBLICATIONS

Zapp et al, "Radiation-Induced Crosslinking of Chlorobutyl and Polydiene Elastomers. Promotion by Polythiols," Rubber Chemistry and Technology, vol. 48, pp. 860-877.
International Search Report, PCT/US2011/046186, dated Dec. 22, 2011, 3 pages.
U.S. Appl. No. 14/608,782, filed Jan. 29, 2015 entitles Mercaptanized Vinylnorbornene Compositions and Methods of Making Same.
U.S. Appl. No. 14/821,835, filed Aug. 10, 2015 entitled Methods of Mercaptanizing Olefinic Hydrocarbons and Compositions Produced Therefrom.
U.S. Appl. No. 14/822,957, filed Aug. 11, 2015 entitled Methods of Mercaptanizing Olefinic Hydrocarbons and Compositions Produced Therefrom.

* cited by examiner

*Primary Examiner* — Duc Truong
(74) *Attorney, Agent, or Firm* — Merchant & Gould P.C.

(57) ABSTRACT

The present invention discloses processes for forming polythiol compositions from olefinic hydrocarbons such as cyclooctadiene, cyclododecatriene, and trivinylcyclohexane. The polythiol compositions produced from these processes, including the sulfur-containing compounds of these compositions, also are described.

21 Claims, No Drawings

METHODS OF MERCAPTANIZING OLEFINIC HYDROCARBONS AND COMPOSITIONS PRODUCED THEREFROM

This application is a divisional application of U.S. patent application Ser. No. 13/891,224, filed on May 10, 2013, now U.S. Pat. No. 9,133,370, which is a divisional application of U.S. patent application Ser. No. 12/849,072, filed on Aug. 3, 2010, now U.S. Pat. No. 8,461,293, the disclosures of which are incorporated herein by reference in their entirety.

BACKGROUND OF THE INVENTION

The present invention relates generally to processes for producing polythiol compositions, and the compositions produced from these processes.

Polythiol compositions disclosed herein can be used as curing agents in adhesive and other applications.

SUMMARY OF THE INVENTION

Processes for forming polythiol compositions are disclosed herein. In accordance with embodiments of the present invention, one such process comprises:
1) contacting
   a) a hydrocarbon compound having at least two olefinic double bonds;
   b) $H_2S$; and
   c) a phosphite compound; and
2) forming the polythiol composition.

In this process, the molar ratio of $H_2S$ to olefinic double bond of the hydrocarbon compound can be in a range from 10:1 to 500:1.

Embodiments of this invention also are directed to polythiol compositions comprising sulfur-containing compounds produced by the disclosed processes.

Further, polythiol compositions derived from hydrocarbon compounds having at least two olefinic double bonds—for instance, compounds such as cyclooctadiene, cyclododecatriene, and trivinylcyclohexane—are disclosed. These polythiol compositions comprise sulfur-containing compounds, and the specific sulfur-containing compounds and their relative presence within the respective polythiol compositions are described.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a system preparation consisting of specific components; alternatively, consisting essentially of specific components; or alternatively, comprising the specific components and other non-recited components.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a hydrocarbon compound having at least two olefinic double bonds," "a phosphite compound," etc., is meant to encompass one, or mixtures or combinations of more than one, hydrocarbon compound having at least two olefinic double bonds, phosphite compound, etc., unless otherwise specified.

For any particular compound or group disclosed herein, any name or structure presented is intended to encompass all conformational isomers, regioisomers, stereoisomers, and mixtures thereof that may arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be an acyclic or cyclic group, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane groups, cycloalkyl, cycloalkylene, cycloalkane groups, alkylaryl/arylalkyl, aralkylene, and aralkane groups, respectively, amongst other groups as members.

The term "hydrocarbon compound having at least two olefinic double bonds" is used herein in accordance with the definitions specified by IUPAC. The hydrocarbon group contains only atoms of carbon and hydrogen. Olefinic double bonds (i.e., —C═C—) are non-aromatic double bonds, but the olefinic double bonds may be either conjugated or non-conjugated, and may be located at any position (e.g., terminally or internally) in the hydrocarbon compound, unless specified otherwise or the context requires otherwise. Thus, by way of example, benzene would not be considered a "hydrocarbon compound having at least two olefinic double bonds," while divinylbenzene would be considered a "hydrocarbon compound having at least two olefinic double bonds."

An aliphatic compound is an acyclic or cyclic, saturated or unsaturated compound, excluding aromatic compounds. That is, an aliphatic compound is a non-aromatic organic compound. Aliphatic compounds, and therefore aliphatic groups, may contain organic functional group(s) and/or atom(s) other than carbon and hydrogen. An "aliphatic group" is a generalized group formed by removing one or more hydrogen atoms (as necessary for the particular group) from a carbon atom of an aliphatic compound.

The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be an acyclic or cyclic group, and/or may be linear or branched, unless otherwise specified. Primary, secondary, or tertiary alkyl groups are derived by removal of a hydrogen atom from a primary, secondary, or tertiary carbon atom, respectively, of an alkane. The n-alkyl group is derived by removal of a hydrogen atom from a terminal carbon atom of a linear alkane. The groups $RCH_2$ (R≠H), $R_2CH$ (R≠H), and $R_3C$ (R≠H) are primary, secondary, and tertiary alkyl groups, respectively.

A cycloalkane is a saturated cyclic hydrocarbon, with or without side chains, for example, cyclobutane and methylcyclobutane. Unsaturated cyclic hydrocarbons having one endocyclic double or one triple bond are called cycloalkenes and cycloalkynes, respectively. Those having more than one such multiple bond are cycloalkadienes, cycloalkatrienes, and so forth.

A "cycloalkyl group" is a univalent group derived by removing a hydrogen atom from a ring carbon atom from a cycloalkane. For example, a 1-methylcyclopropyl group and a 2-methylcyclopropyl group are illustrated as follows:

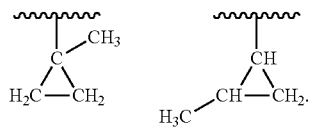

Similarly, a "cycloalkylene group" refers to a group derived by removing two hydrogen atoms from a cycloalkane, at least one of which is a ring carbon. Thus, a "cycloalkylene group" includes a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane.

As used herein, a "polythiol composition" refers to a composition comprising sulfur-containing compounds having two or more thiol groups per molecule (e.g., 2, 3, 4, 5, etc., thiol groups). For illustrative purposes, a mercaptanized cyclododecatriene composition, or a polythiol composition derived from cyclododecatriene, can comprise dimercaptocyclododecene and trimercaptocyclododecane, among other compounds having two or more thiol groups, but the composition also may contain compounds having only one thiol group (e.g., monomercaptocyclododecadiene). Furthermore, such polythiol compositions may contain other compounds; one non-limiting example may be the residual or unreacted hydrocarbon compound having two or more olefinic double bonds (e.g., cyclododecatriene in the case of a polythiol composition derived from cyclododecatriene).

In some instances, the polythiol composition derived from a hydrocarbon compound having at least two olefinic double bonds may be described, while in others, the organic sulfur-containing compounds of the polythiol composition may be described. Consequently, within this disclosure, properties associated with the polythiol compositions may include contributions from the hydrocarbon compound from which the compositions were formed, as well as other reactants and by-products. In some circumstances, it may be beneficial to refer only to the sulfur-containing compounds derived from the hydrocarbon compound, as if the hydrocarbon compound, other reactants, by-products, and/or solvent are not present in the composition. Within this disclosure, the term "sulfur-containing compounds" used in conjunction with the polythiol composition refers to compounds within the composition that contain sulfur (e.g., thiol sulfur, sulfide sulfur) and are formed from or ultimately formed from the hydrocarbon compound having at least two olefinic double bonds, and excludes any non-sulfur-containing compound (e.g., reactant hydrocarbon compound and/or solvent, among others), any sulfur-containing reactant (e.g., $H_2S$), and any sulfur-containing compound not formed, or not ultimately formed, from the hydrocarbon compound having at least two olefinic double bonds. In instances where weight percentages of sulfur-containing compounds of the polythiol composition are described, the total of the sulfur-containing hydrocarbons will equal 100%. In sum, a "polythiol composition" can include all materials in a composition comprising polythiol compounds, while the "sulfur-containing compounds" refer only to the compounds within the polythiol composition which are formed, or ultimately formed, from the hydrocarbon compound having at least two olefinic double bonds.

The terms "contact product," "contacting," and the like, are used herein to describe compositions wherein the components are contacted together in any order, in any manner, and for any length of time. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. These include, but are not limited to, a range of number of atoms, a range of weight ratios or percentages, a range of molar ratios, a range of temperatures, a range of contact or reaction times, a range of reactor pressures, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a hydrocarbyl group having from 1 to 18 carbon atoms (i.e., a $C_1$-$C_{18}$ hydrocarbyl group), as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a hydrocarbyl group having 3 to 8 carbon atoms), and also including any combination of ranges between these two numbers (for example, a hydrocarbyl group having 1 to 4 carbon atoms and a hydrocarbyl group having 8 to 12 carbon atoms).

Similarly, another representative example follows for the molar ratio of $H_2S$ to olefinic double bond of the hydrocarbon compound provided in an embodiment of this invention. By a disclosure that the molar ratio of $H_2S$ to olefinic double bond of the hydrocarbon compound is in a range from 35:1 to 150:1, Applicants intend to recite that the molar ratio can be 35:1, about 40:1, about 45:1, about 50:1, about 55:1, about 60:1, about 65:1, about 70:1, about 75:1, about 80:1, about 85:1, about 90:1, about 95:1, about 100:1, about 105:1, about 110:1, about 115:1, about 120:1, about 125:1 about 130:1, about 135:1 about 140:1, about 145:1, or 150:1. Additionally, the molar ratio can be within any range from 35:1 to 150:1 (for example, the molar ratio is in a range from about 50:1 to about 100:1), and this also includes any combination of ranges between 35:1 and 150:1. Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

DETAILED DESCRIPTION OF THE INVENTION

The present invention provides methods of mercaptanizing olefinic hydrocarbons, and polythiol compositions produced therefrom.

Mercaptanizing Olefinic Hydrocarbons to Produce Polythiol Compositions

Embodiments of this invention are directed to processes for forming a polythiol composition. Such processes can comprise:
1) contacting
   a) a hydrocarbon compound having at least two olefinic double bonds;
   b) $H_2S$; and
   c) a phosphite compound; and
2) forming the polythiol composition.

Generally, the features of the process (e.g., the hydrocarbon compound, the phosphite compound, the hydrogen sulfide to olefin double bond ratio, the components of and/or features of the polythiol composition, and the conditions under which the polythiol composition is formed, among others) are independently described herein and these features may be combined in any combination to further describe the process.

In some embodiments, the contacting step (step 1 of the process) may include contacting the hydrocarbon compound, $H_2S$, the phosphite compound, and additional unrecited materials (e.g., a solvent). In other embodiments, the contacting step may consist essentially of contacting the hydrocarbon compound, $H_2S$, and the phosphite compound or, alternatively, consist of contacting the hydrocarbon compound, $H_2S$, and the phosphite compound. Likewise, additional materials or features may be employed in the forming step (step 2 of the process). For instance, the formation of the polythiol composition may occur in the presence of ultraviolet light, to be discussed further below. Further, it is contemplated that the processes for forming polythiol compositions can employ more than one hydrocarbon compound and/or more than one phosphite compound. Hydrocarbon compounds having at least two olefinic double bonds and phosphite compounds are described herein and these materials may be utilized without limitation in the processes.

In the processes disclosed herein, the molar ratio of $H_2S$ to olefinic double bond of the hydrocarbon compound can be in a range from 10:1 to 500:1, or from 15:1 to 500:1, or from 20:1 to 500:1. In some embodiments, the molar ratio of $H_2S$ to olefinic double bond of the hydrocarbon compound can be in a range from 30:1 to 500:1, while in other embodiments, the molar ratio of $H_2S$ to olefinic double bond of the hydrocarbon compound can be in a range from 40:1 to 500:1. Molar ratios of $H_2S$ to olefinic double bond of the hydrocarbon compound falling within the range from 25:1 to 500:1, or from 35:1 to 250:1, or from 40:1 to 250:1, or from 50:1 to 250:1, or from 35:1 to 150:1, or from 40:1 to 150:1, or from 50:1 to 150:1, also can be employed in embodiments of this invention While not limited thereto, the molar ratio of the phosphite compound to olefinic double bond of the hydrocarbon compound can be in a range from 0.0025:1 to 1:1, or from 0.003:1 to 0.10:1, or from 0.004:1 to 0.07:1, or from 0.005:1 to 0.05:1. In some embodiments, the molar ratio of the phosphite compound to olefinic double bond of the hydrocarbon compound can be in a range from 0.006:1 to 0.05:1; alternatively, from 0.006:1 to 0.04:1; alternatively, from 0.007:1 to 0.04:1; or alternatively, from 0.007:1 to 0.03:1.

Independently, steps 1 and 2 of the process for forming a polythiol composition can be conducted at a variety of temperatures, pressures, and time periods. For instance, the temperature at which the hydrocarbon compound, $H_2S$, and the phosphite compound are initially contacted can be the same as, or different from, the temperature at which the polythiol composition is formed. As an illustrative example, in step 1, the hydrocarbon compound, $H_2S$, and the phosphite compound can be contacted initially at temperature T1 and, after this initial combining, the temperature can be increased to a temperature T2 to allow the formation of the polythiol composition. Likewise, the pressure may be different in step 1 than in step 2. Often, the time period in step 1 is referred to as the contact time, while the time period in step 2 is referred to as the reaction time. The contact time and the reaction time can be, and usually are, different.

In an embodiment, step 1 of the process for forming a polythiol composition can be conducted at a temperature in a range from 0° C. to 120° C.; alternatively, from 10° C. to 110° C.; alternatively, from 15° C. to 100° C.; alternatively, from 20° C. to 80° C.; alternatively, from 20° C. to 50° C.; or alternatively, from 25° C. to 45° C. In these and other embodiments, after the initial contacting, the temperature can be changed, if desired, to another temperature for the formation of the polythiol composition. Accordingly, step 2 can be conducted at a temperature in a range from 0° C. to 120° C.; alternatively, from 10° C. to 110° C.; alternatively, from 15° C. to 100° C.; alternatively, from 20° C. to 100° C.; alternatively, from 20° C. to 80° C.; or alternatively, from 25° C. to 80° C. These temperature ranges also are meant to encompass circumstances where the forming step can be conducted at a series of different temperatures, instead of at a single fixed temperature, falling within the respective ranges.

In an embodiment, step 1 and/or step 2 of the process of forming a polythiol composition can be conducted at a total reactor pressure in a range from 30 to 1500 psig, such as, for example, from 50 to 1500 psig. In some embodiments, the polythiol formation in step 2 can be conducted at total reactor pressure in a range from 50 to 1500 psig; alternatively, from 50 to 1000 psig; alternatively, from 50 to 750 psig; alternatively, from 50 to 500 psig; or alternatively, from 100 to 500 psig.

The contact time in step 1 of the process is not limited to any particular range. That is, the hydrocarbon compound, $H_2S$, and the phosphite compound can be initially contacted rapidly, or over a longer period of time, before commencing the reaction and/or the formation of the polythiol composition in step 2. Hence, step 1 can be conducted, for example, in a time period ranging from as little as about 1-30 seconds to as long as about 1-6 hours. In some embodiments, the contact time can be in a range from 15 minutes to 3 hours, or from 30 minutes to 2 hours. The appropriate reaction time for the formation of the polythiol composition in step 2 can depend upon, for example, the reaction temperature and the molar ratios of the respective components in step 1, among other variables. However, the polythiol may be formed over a time period in step 2 that can be in a range from 1 minute to 8 hours, such as, for example, from 2 minutes to 6 hours, from 5 minutes to 5 hours, from 10 minutes to 4 hours, or from 15 minutes to 3 hours.

In embodiments of this invention, once the hydrocarbon compound, $H_2S$, and the phosphite compound are contacted, the polythiol composition may be formed in the presence of ultraviolet light. Additionally or alternatively, the polythiol composition may be formed by light photolysis initiation of a free radical initiator. Additionally or alternatively, the polythiol composition may be formed under conditions suitable for the thermal decomposition of a free radical initiator. Additionally, a photoinitiator may be utilized in conjunction with ultraviolet light or light photolysis initiation of a free radical initiator. Free radicals, therefore, may be generated in situ by a suitable energy source, or may be generated by the thermal decomposition of a free radical initiator, or by a combination of these sources. The polythiol composition may be formed in the presence of free radicals from any one of aforementioned sources, including combinations thereof, but is not limited to free radicals generated only by these means.

In an embodiment, the step 1 contacting of the hydrocarbon compound, $H_2S$, and the phosphite compound can be conducted prior to the generation of free radicals and the formation of the polythiol composition in step 2.

When the polythiol composition is formed in the presence of ultraviolet light, ultraviolet light in the range, for example, from 172 to 450 nm, from 172 to 380 nm, or from 172 to 320 nm, may be employed. Ultraviolet light can be supplied from ultraviolet lamps, but other sources of ultraviolet light may be employed, and are to be considered within the scope of the present invention.

The free radical initiator may be any free radical initiator capable of forming free radicals under thermal decomposition or light photolysis. For example, the free radical initiator employed for the formation of the polythiol composition can comprise a —N═N— group, a —O—O— group, or combinations thereof; alternatively, a —N═N— group; or alternatively, a —O—O— group. Free radical initiators, therefore, can include, but are not limited, to peroxy compounds, organic azo compounds, and the like, or combinations thereof; alternatively, peroxy compounds; or alternatively, organic azo compounds. Peroxy compounds which may be utilized can include peroxides, hydroperoxides, peroxyesters, diacylperoxides, and percarbonates; alternatively, peroxides; alternatively, hydroperoxides; alternatively, peroxyesters; alternatively, diacylperoxides; or alternatively, percarbonates. In an embodiment, the peroxide which may be utilized can be a dialkyl peroxide. In an embodiment, the hydroperoxide which may be utilized can be an alkyl hydroperoxide. In an embodiment, the peroxy ester which may be utilized can be an alkyl peroxyalkanoate; or alternatively, an alkyl peroxyarenoate. In an embodiment, the diacylperoxide may be a diaroyl peroxide; or alternatively, a diakoyl peroxide. In an embodiment, the percarbonate which may be utilized can be a dihydrocarbyl percarbonate; alternatively, a diarylpercarbonate; or alternatively, a dialkylpercarbonate. Generally, the hydrocarbon and/or alkane group(s) utilized in any peroxy compound can be a $C_1$ to $C_{30}$, $C_2$ to $C_{20}$, $C_2$ to $C_{10}$, or $C_2$ to $C_5$ hydrocarbon and/or alkane group(s). Generally, the arene group utilized in any peroxy compound can be a $C_6$ to $C_{30}$, $C_6$ to $C_{20}$, $C_6$ to $C_{15}$, or $C_6$ to $C_{10}$ arene group(s). Illustrative non-limiting examples of peroxy compounds which may be utilized can include, but are not limited to, diisobutyryl peroxide, 1-(2-ethylhexanoylperoxy)-1,3-dimethylbutyl peroxypivalate, cumylperoxyneodecanoate, 1,1,3,3-tetramethylbutyl peroxyneodecanoate, t-butyl peroxyneodecanoate, 1,1,3,3-tetramethylbutyl peroxypivalate, t-butyl peroxyneoheptanoate, t-amyl peroxypivalate, t-butyl peroxypivalate, di(3,5,5-trimethylhexanoyl)peroxide, dilauroyl peroxide, didecanoyl peroxide, 2,5-dimethyl-2,5-di(2-ethylhexanoylperoxy)hexane, 1,1,3,3-tetramethylbutyl peroxy 2-ethylhexanoate, t-amyl peroxy 2-ethylhexanoate, dibenzoyl peroxide, acetyl peroxide t-butyl peroxy 2-ethylhexanoate, t-butyl peroctanoate, t-butyl peroxydiethylacetate, t-butyl peroxyisobutyrate, t-butyl peroxy 3,5,5-trimethylhexanoate, t-butyl peroxyacetate, t-butyl peoxybenzoate, 2,4-dichlorobenzoyl peroxide, t-butylpermaleic acid, di-t-butyl diperphthalate, di(4-t-butylcyclohexyl) peroxydicarbonate, di(2-ethylhexyl) peroxydicarbonate, dibutyl peroxydicarbonate, dicetyl peroxydicarbonate, dimyristyl peroxydicarbonate, t-amylperoxy 2-ethylhexyl carbonate, t-butylperoxy isopropyl carbonate, t-butylperoxy 2-ethylhexyl carbonate, 1,1-di(t-butylperoxy) 3,5,5-trimethylcyclohexane, 2,2-di(4,4-di(t-butylperoxy)-cyclohexyl)propane, 1,1-di(t-butylperoxy)cyclohexane, 2,2-di(t-butylperoxy)butane, di(t-amyl) peroxide, dicumyl peroxide, di(t-butylperoxyisopropyl) benzene, 2,5-dimethyl-2,5-di(t-butylperoxy)hexane, t-butyl cumyl peroxide, 2,5-dimethyl-2,5-di(t-butylperoxy)hexyne-3, di-t-butyl peroxide, 3,6,9-triethyl-3,6,9-trimethyl-1,4,7-triperoxoane, t-butyl hydroperoxide, methyl benzyl hydroperoxide, octylperbenzoate, methyl ethyl ketone peroxide, acetone peroxide, and the like, or combinations thereof.

Non-limiting examples of suitable azo compounds include α,α'-azo diisobutyronitrile (AIBN), azobenzene, azomethane, 2,2'-azodi(2-methylbutyronitrile), 2,2'-azobis (4-methoxy-2,4-dimethyl valeronitrile), dimethyl 2,2'-azobis (2-methylpropionate), 1,1'-azobis-(cyclohexane-1-carbonitrile), 1-[(cyano-1-methylethyl)azo]formamide, 2,2'-azobis (N-cyclohexyl-2-methylpropionamide), 2,2'-azobis(2,4-dimethyl valeronitrile), 2,2'-azobis(2-methylbutyronitrile), 2,2'-azobis[N-(2-propenyl)-2-methylpropionamide], 2,2'-azobis(N-butyl-2-methylpropionamide), 2,2'-azobis{2-methyl-N-[1,1-bis(hydroxymethyl)-2-hydroxyethyl]propionamide, 2,2'-azobis[2-methyl-N-(2-hydroxyethyl) propionamide], 2,2'-azobis[2-(2-imidazolin-2-yl)propane], 2,2'-azobis{2-methyl-N-[2-(1-hydroxybutyl)]propionamide}, 2,2'-azobis(2-methylpropionitrile), 4,4'-azobis(4-cyanovaleric acid), 2,2'-azobis(2-methylpropane), 2,2'-azobis (2-methylpropionamidine)dihydrochloride, methylpropionitrile, azodicarboxamide, and the like, or combinations thereof.

Generally, the peroxide and azo compound free radical initiators that can be utilized in accordance with the present invention decompose under first order kinetics. Skilled artisans can readily find the first order kinetic parameters which can be utilized to describe the decomposition of a particular free radical catalyst from sources such as chemical suppliers, industry reference publications, and/or open literature publications. Under first order kinetics, the time required for a given fraction (or percentage) of the free radical initiator to decompose, at a specific temperature, into initiating species is independent of the concentration of the free radical. This phenomenon is often stated as a half-life; that is, the time in which one-half of the free radical initiator decomposes under specific conditions (e.g., temperature). According to the first order kinetics, the half-life of a free radical initiator is defined as the time it takes one-half of the initiator to decompose at a particular temperature. Using the available first order kinetic parameters for a particular free radical initiator, the concentration of the free radical initiator present in the reaction mixture may be determined at a particular time during the reaction based upon the knowledge of the amount of free radical initiator added to the reaction, the times at which additional (if any) free radical initiator is added to the reaction, and the temperature profile of the reaction.

When the polythiol composition is formed under conditions utilizing the thermal decomposition of a free radical initiator, the polythiol composition may be formed at a temperature within a temperature range of the 1 hour half-life of the free radical initiator. Alternatively, when the polythiol composition is formed under conditions utilizing the thermal decomposition of a free radical initiator, the polythiol composition may be formed using a free radical initiator having a half-life within a time range at the temperature utilized to form the polythiol composition. For example, step 2 of the process (the formation of the polythiol composition) can be conducted at a temperature within ±25° C. of the 1 hour half-life of the free radical initiator. In other embodiments, the polythiol composition can be formed at a temperature within ±20° C. of the 1 hour half-life of the free radical initiator; alternatively, at a temperature within ±15° C. of the 1 hour half-life of the free radical initiator; alternatively, at a temperature within ±10° C. of the 1 hour half-life of the free radical initiator. In another embodiment, the polythiol composition can be formed using a free radical initiator having a half-life within a range from 0.1 to 10 hours at the temperature the polythiol composition is formed (i.e., in step 2 of the process). Alternatively, the polythiol composition can be formed using a free radical initiator having a half-life ranging from 0.1 to 10 hours, from 0.25 to 4 hours, or from 0.5 to 2 hours, at the temperature the polythiol composition is formed. As above, in some embodiments of this invention, the polythiol composition can be formed at a temperature in a range from 0° C. to 120° C.; alternatively, from 10° C. to 110° C.; alternatively, from 15° C. to 100° C.; alternatively, from 20° C. to 100° C.; alternatively, from 20° C. to 80° C.; or alternatively, from 25° C. to 80° C.

Depending upon the particular free radical initiator, a free radical initiator can produce a different number of free radical reaction-initiating species per mole of free radical initiator; thus, the concentration of the free radical initiator can be stated in terms which describe the number of free radical reaction-initiating species generated per mole of free radical initiator. The term "equivalent" is often used to describe the number of reaction-initiating species produced per mole of free radical initiator. For example, one skilled in the art will readily recognize that di-t-butylperoxide can generate two free radical reaction-initiating species per mole of di-t-butylperoxide, while 2,5-bis(t-butylperoxy)-2,5-dimethylhexane can generate four free radical reaction-initiating species per mole of 2,5-bis(t-butylperoxy)-2,5-dimethylhexane.

In an embodiment, a photoinitiator may be utilized. Commercially available photoinitiators include, by way of example, Irgacure® 184 (1-hydroxy-cyclohexyl-phenyl-ketone), Irgacure® 500 (50% 1-hydroxy-cyclohexyl-phenyl-ketone and 50% benzophenone), Irgacure® 819 (Bis-(2,4,6-trimethylbenzoyl)-phenylphosphineoxide), and Irgacure® 127 (2-hydroxy-1-{4-[4-(2-hydroxy-2-methyl-propionyl)-benzyl]-phenyl}-2-methyl-propan-1-one), all available from Ciba Specialty Chemicals, and Duracure 1173 (2-hydroxy-2-methyl-1-phenyl-1-propanone).

When a free radical initiator is present in step 1 and/or in step 2 of the process, the weight percentage of the free radical initiator, based on the weight of the hydrocarbon compound, can be in a range from 0.5 to 10 wt. %, from 0.75 to 9 wt. %, from 1 to 8 wt. %, or from 1.5 to 7 wt. %. When a photoinitiator is present in step 1 and/or in step 2 of the process, the weight percentage of the photoinitiator, based on the weight of the hydrocarbon compound, can be in a range from 0.01 to 2 wt. %, from 0.025 to 1.5 wt. %, from 0.05 to 1 wt. %, or from 0.075 to 0.75 wt. %. Other amounts of the free radical initiator and/or the photoinitiator may be employed depending on the specific process conditions used to form the polythiol composition (e.g., temperature, pressure, time) and the respective ratios of $H_2S$ to hydrocarbon compound and of phosphite compound to hydrocarbon compound, amongst other factors. It is contemplated that more than one free radical initiator, more than one photoinitiator, or combinations of free radical initiator(s) and photoinitiator(s), can be employed.

In an embodiment, the polythiol composition can be formed in the absence of a solvent. However, in other embodiments, the polythiol can be formed in the presence of a solvent. Typically, when used, the solvent may be present in an amount up to 1,000 wt. %, based on the weight of the hydrocarbon compound having at least two olefinic double bonds. Alternatively, the formation of the polythiol may be performed in the presence of a solvent in an amount up 750 wt. %, up to 500 wt. %, up to 250 wt. %, up to 200 wt. %, up to 150 wt. %, or up to 100 wt. %. When a solvent is utilized, the minimum amount of solvent that may be utilized may be at least 5 wt. %, at least 10 wt. %, at least 25 wt. %, at least 50 wt. %, or at least 75 wt. %, based on the weight of the hydrocarbon compound. Generally, the range of solvent which may be utilized may range from any minimum amount of solvent disclosed herein to any maximum amount of solvent disclosed herein. In some non-limiting embodiments, the formation of the polythiol may be performed in the presence of a solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the hydrocarbon compound. The organic solvent may be contacted with the hydrocarbon compound, $H_2S$, and the phosphite compound in step 1 of the process, and remain present during the formation of the polythiol composition. Alternatively, the organic solvent may be added after the initial contacting in step 1. Organic solvents which may be utilized as the solvent are described herein, and these organic solvents may be utilized without limitation in the processes described herein.

In the processes for producing a polythiol composition disclosed herein, it is contemplated that at least 60% of the olefinic double bonds of the hydrocarbon compound have reacted to form a sulfur-containing group in the polythiol composition. Often, at least 65% of the olefinic double bonds of the hydrocarbon compound have reacted to form a sulfur-containing group; alternatively, at least 70%; alternatively; at least 75%; alternatively, at least 80%; alternatively, at least 85%; alternatively, at least 90%; alternatively, at least 95%; alternatively, at least 98%; or alternatively, at least 99%.

Once formed, the polythiol composition, or specific fractions of the polythiol composition, can be purified and/or isolated and/or separated using suitable techniques which include, but are not limited to, evaporation, distillation, crystallization, extraction, washing, decanting, filtering, drying, and the like, including combinations of more than one of these techniques. In one embodiment, the process for producing a polythiol composition can further comprise a step of separating or removing at least a portion of the $H_2S$, of the phosphite compound, of the hydrocarbon compound, of compounds having only one sulfur atom, or any combination thereof, from the polythiol composition. For instance, these materials can be separated or removed by distillation, by short path distillation, by wiped film evaporation, or by a combination of these techniques.

Hydrocarbon Compound

Embodiments of this invention are directed to processes for forming a polythiol composition, and these processes can comprise contacting a hydrocarbon compound having at least two olefinic double bonds, $H_2S$, and a phosphite compound; and forming the polythiol composition. Generally, the molar ratio of $H_2S$ to olefinic double bond of the hydrocarbon compound is in a range from 10:1 to 500:1, from 20:1 to 500:1, or from 40:1 to 500:1.

The hydrocarbon compound used in these processes has at least two olefinic double bonds. In one embodiment, the hydrocarbon compound has from 2 to 10 olefinic double bonds; alternatively, from 2 to 8 olefinic double bonds; alternatively, from 2 to 6 olefinic double bonds; or alternatively, from 2 to 4 olefinic double bonds. In another embodiment, the hydrocarbon compound has only two olefinic double bonds; alternatively, only three olefinic double bonds; alternatively, only four olefinic double bonds; alternatively, only five olefinic double bonds; or alternatively, only six olefinic double bonds.

Suitable examples of hydrocarbon compounds having at least two olefinic double bonds that may be employed in the processes disclosed herein include, but are not limited to, butadiene, isoprene, cyclobutadiene, cyclopentadiene, cyclohexadiene, cyclooctadiene, norbornadiene, vinylcyclohexene, vinylnorbornene, divinylbenzene, cyclopentadiene dimer, and the like, or any combination thereof. Mixtures or combinations of more than one hydrocarbon compound having at least two olefinic double bonds can be employed. Accordingly, the hydrocarbon compound having at least two olefinic double bonds can comprise, consist essentially of, or consist of, butadiene, isoprene, cyclobutadiene, cyclopentadiene, cyclohexadiene, cyclooctadiene, or combinations thereof; alternatively, norbornadiene, vinylcyclohexene, vinylnorbornene, divinylbenzene, or combinations thereof; alternatively, butadiene; alternatively, isoprene; alternatively, cyclobutadiene; alternatively, cyclopentadiene; alternatively, cyclohexadiene; alternatively, cyclooctadiene; alternatively, norbornadiene; alternatively, vinylcyclohexene; alternatively, vinylnorbornene; alternatively, divinylbenzene; or alternatively, cyclopentadiene dimer.

In an embodiment, the hydrocarbon compound can comprise, consist essentially of, or consist of, one or more compounds having only three olefinic double bonds. Illustrative non-limiting examples of such compounds can comprise, consist essentially of, or consist of, trivinylcyclohexane, trivinylbenzene, cycloheptatriene, dimethyl heptatriene, octatriene, cyclooctatriene, cyclododecatriene, including mixtures and/or combinations thereof. In one embodiment, the hydrocarbon compound having only three olefinic double bonds can comprise, consist essentially of, or consist of, trivinylcyclohexane. In another embodiment, the hydrocarbon compound having only three olefinic double bonds can comprise, consist essentially of, or consist of, trivinylbenzene. In another embodiment, the hydrocarbon compound can comprise, consist essentially of, or consist of, cycloheptatriene. In another embodiment, the hydrocarbon compound having only three olefinic double bonds can comprise, consist essentially of, or consist of, dimethyl heptatriene. In another embodiment, the hydrocarbon compound having only three olefinic double bonds can comprise, consist essentially of, or consist of, octatriene. Yet, in another embodiment, the hydrocarbon compound having only three olefinic double bonds can comprise, consist essentially of, or consist of, cyclooctatriene. In still another embodiment, the hydrocarbon compound having only three olefinic double bonds can comprise, consist essentially of, or consist of, cyclododecatriene.

Hydrocarbon compounds having four or more olefinic bonds also are contemplated. For instance, the hydrocarbon compound having four or more olefinic bonds can comprise, consist essentially of, or consist of, cyclooctatetraene; alternatively, cyclododecatetraene; alternatively, a polybutadiene; or alternatively, a combination of two or more of these olefinic hydrocarbons.

Additionally, olefin metathesis products having two or more olefinic bonds can be utilized. As such, the hydrocarbon compound having two or more olefinic bonds can comprise, consist essentially of, or consist of, an olefin metathesis product of one or more of the following representative compounds: vinylcyclohexene, vinylnorbornene, divinylbenzene, trivinylcyclohexane, trivinylbenzene, norbornene, norbornadiene, cyclooctadiene, trivinylcyclohexane, and cyclododecatriene. For instance, the hydrocarbon compound having two or more olefinic bonds can comprise, consist essentially of, or consist of, an olefin metathesis product of vinylcyclohexene, an olefin metathesis product of vinylcyclohexene with vinylnorbornene, and so forth.

In an embodiment, the hydrocarbon compound having two or more olefinic bonds can comprise, consist essentially of, or consist of, an unsaturated hydrocarbon terpene compound having at least two olefinic double bonds. For example, the hydrocarbon compound having two or more olefinic bonds can comprise, consist essentially of, or consist of, a monoterpene, a sesquiterpene, a diterpene, a sesterpene, a triterpene, and the like, or any combination thereof. Accordingly, the hydrocarbon compound can comprise, consist essentially of, or consist of, a monoterpene, a sesquiterpene, or any combination thereof; alternatively, a monoterpene; alternatively, a sesquiterpene; alternatively, a diterpene; alternatively, a sesterpene; or alternatively, a triterpene. The unsaturated hydrocarbon terpene can comprise, consist essentially of, or consist of, a cyclic terpene in some embodiments of this invention, while in other embodiments, the hydrocarbon terpene can comprise, consist essentially of, or consist of, an acyclic terpene.

The hydrocarbon compound having two or more olefinic bonds can comprise, consist essentially of, or consist of, myrcene, ocimene (i.e., (E)-ocimene, (Z)-ocimene, or mixtures thereof), alloocimene, cosmene, limonene, terpinolene, terpinene (i.e., α-terpinene, γ-terpinene, or mixtures thereof), phellandrene (i.e., α-phellandrene, β-phellandrene, or mixtures thereof), 1,3,8-para-menthatriene, and the like, or any combination thereof; alternatively, myrcene; alternatively, ocimene; alternatively, alloocimene; alternatively, cosmene; alternatively, limonene; alternatively, terpinolene, alternatively, terpinene; alternatively, phellandrene; or alternatively, 1,3,8-para-menthatriene. Yet, in other embodiments, the hydrocarbon compound having two or more olefinic bonds can comprise, consist essentially of, or consist of, farnesene (i.e., (E)-α-farnesene, (Z)-α-farnesene, (E)-(β-farnesene, (Z)-(β-farnesene, or mixtures thereof), bisabolene (i.e., α-bisabolene, (β-bisabolene, or mixtures thereof), zingiberene, β-curcumene, laurene, elemene (i.e., α-elemene, (β-elemene, or mixtures thereof), humulene, germacrene, cadinene (i.e., α-cadinene, (β-cadinene, γ-cadinene, or mixtures thereof), selinene (i.e., α-selinene, β-selinene, or mixtures thereof), eremophilene, nootkatene, valencene, and the like, or any combination thereof; alternatively, farnesene; alternatively, bisabolene; alternatively, zingiberene; alternatively, β-curcumene; alternatively, laurene; alternatively, elemene; alternatively, humulene; alternatively, germacrene; alternatively, cadinene; alternatively, selinene; alternatively, eremophilene; alternatively, nootkatene; or alternatively, valencene.

In accordance with another embodiment, the hydrocarbon compound having two or more olefinic bonds can comprise, consist essentially of, or consist of, cembrene, abietadiene, casbene, haslene, squalene, or any combination thereof. Combinations of two or more of these materials can be employed (e.g., cembrene and casbene). Additionally, each of these materials can be employed singularly; for example, the hydrocarbon compound having two or more olefinic bonds can comprise, consist essentially of, or consist of, haslene; alternatively, the hydrocarbon compound having two or more olefinic bonds can comprise, consist essentially of, or consist of, squalene.

Phosphite Compound

Generally, the phosphite compound employed in the processes for forming a polythiol composition disclosed herein can comprise, consist essentially of, or consist of, a trihydrocarbylphosphite compound. Each hydrocarbyl group, independently, in the trihydrocarbylphosphite compound can be a $C_1$-$C_{36}$ hydrocarbyl group; alternatively, a $C_1$-$C_{18}$ hydrocarbyl group; alternatively, a $C_1$-$C_{12}$ hydrocarbyl group; or alternatively, a $C_1$-$C_8$ hydrocarbyl group. Each hydrocarbyl group, independently, in the trihydrocarbylphosphite compound can be an alkyl group, an alkenyl group, an aryl group, or an alkylaryl/arylalkyl group. Alkyl groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl; alternatively, methyl, ethyl, propyl, butyl, pentyl, hexyl, heptyl, octyl, nonyl, decyl, undecyl, or dodecyl; or alternatively, methyl, ethyl, propyl, butyl, pentyl, hexyl, heptyl, or octyl. Alkenyl groups include, but are not limited to, ethenyl, propenyl, butenyl, pentenyl, hexenyl, heptenyl, octenyl, and the like. Aryl and alkylaryl/arylalkyl groups include, but are not limited to, phenyl, alkyl-substituted phenyl, naphthyl, alkyl-substituted naphthyl, phenyl-substituted alkyl, naphthyl-substituted alkyl; alternatively, phenyl or naphthyl; or alternatively, phenyl.

Unless otherwise specified, the disclosure of an alkyl group is intended to include all structural isomers, linear or branched, of a given moiety. Additionally, unless otherwise specified, the disclosure of an alkyl group is intended to include all enantiomers and all diastereomers. As examples, unless otherwise specified, the term propyl is meant to include n-propyl and iso-propyl, the term butyl is meant to include n-butyl, iso-butyl, t-butyl, sec-butyl, and the term octyl includes n-octyl, 2-ethylhexyl and neooctyl, among other isomers. Unless otherwise specified, any aryl group or alkylaryl/arylalkyl group used herein includes all structural isomers (regioisomers, and linear or branched isomers), enantiomers, and diastereomers. For example, the term tolyl is meant to include any possible substituent position, that is, 2-methylphenyl, 3-methylphenyl, and/or 4-methylphenyl, and the term xylyl includes 2,3-dimethylphenyl, 2,4-dimethylphenyl, 2,5-dimethylphenyl, 2,6-dimethylphenyl, 3,4-dimethylphenyl, 3,5-dimethylphenyl, and 3,6-dimethylphenyl.

In an embodiment, each hydrocarbyl group, independently, in the trihydrocarbylphosphite compound can be methyl, ethyl, n-propyl, iso-propyl, n-butyl, iso-butyl, t-butyl, n-pentyl, neo-pentyl, phenyl, benzyl, tolyl, xylyl (dimethylphenyl), trimethylphenyl, phenylethyl, phenylpropyl, phenylbutyl, propyl-2-phenylethyl, or naphthyl. In another embodiment, each hydrocarbyl group, independently, in the trihydrocarbylphosphite compound can be methyl, ethyl, propyl, butyl, pentyl, phenyl, benzyl, tolyl, or xylyl; or alternatively, methyl, ethyl, propyl, butyl, or pentyl. In yet another embodiment, each hydrocarbyl group, independently, in the trihydrocarbylphosphite compound can be phenyl, benzyl, tolyl, or xylyl. In still another embodiment, each hydrocarbyl group in the trihydrocarbylphosphite compound is the same, and is methyl; alternatively, ethyl; alternatively, propyl; alternatively, butyl; alternatively, pentyl; alternatively, phenyl; alternatively, benzyl; alternatively, tolyl; or alternatively, xylyl. For example, the trihydrocarbylphosphite compound can be triphenylphosphite.

The phosphite compound, in certain embodiments, can comprise a compound having the formula:

In this formula, each $R^1$ independently can be a $C_1$-$C_{18}$ hydrocarbyl group; alternatively, a $C_1$-$C_{10}$ hydrocarbyl group; alternatively, a $C_1$-$C_5$ hydrocarbyl group; alternatively, a $C_1$-$C_{18}$ alkyl group; alternatively, a $C_1$-$C_{10}$ alkyl group; alternatively, a $C_1$-$C_5$ alkyl group; alternatively, a $C_2$-$C_{18}$ alkenyl group; alternatively, a $C_3$-$C_{12}$ alkenyl group; alternatively, a $C_3$-$C_6$ alkenyl group; alternatively, a $C_6$-$C_{18}$ aryl group; or alternatively, a $C_6$-$C_{10}$ aryl group. Accordingly, $R^1$ can be a methyl group, an ethyl group, a propyl group, a butyl group, a pentyl group, a hexyl group, a heptyl group, an octyl group, a nonyl group, a decyl group; a propenyl group, a butenyl group, a pentenyl group, a hexenyl group, a heptenyl group, or a octenyl group; alternatively, $R^1$ can be a methyl group, an ethyl group, a propyl group, a butyl group, a pentyl group, a propenyl group, a butenyl group, or a pentenyl group; alternatively, $R^1$ can be a methyl group; alternatively, $R^1$ can be an ethyl group; alternatively, $R^1$ can be a propyl group; alternatively, $R^1$ can be a butyl group; alternatively, $R^1$ can be a pentyl group; alternatively, $R^1$ can be a hexyl group; alternatively, $R^1$ can be a heptyl group; alternatively, $R^1$ can be an octyl group; alternatively, $R^1$ can be a nonyl group; alternatively, $R^1$ can be a decyl group; alternatively, $R^1$ can be a propenyl group; alternatively, $R^1$ can be a butenyl group; alternatively, $R^1$ can be a pentenyl group; alternatively, $R^1$ can be a hexenyl group; alternatively, $R^1$ can be a heptenyl group; or alternatively, $R^1$ can be an octenyl group. In some embodiments, $R^1$ can be a phenyl group, a tolyl group, a xylyl group, or a naphthyl group; alternatively, a phenyl group, a tolyl group, or a xylyl group; alternatively, a phenyl group; alternatively, a tolyl group; alternatively, a xylyl group; or alternatively, a naphthyl group.

In accordance with an embodiment of this invention, the phosphite compound can comprise, consist essentially of, or consist of, a trialkylphosphite; or alternatively, a triarylphosphite. In accordance with another embodiment of this invention, the phosphite compound can comprise, consist essentially of, or consist of, trimethylphosphite, triethylphosphite, tributylphosphite, or combinations thereof. Yet, in accordance with another embodiment of this invention, the phosphite compound can comprise trimethylphosphite; alternatively, triethylphosphite; or alternatively, tributylphosphite. In another embodiment, the phosphite compound can comprise, consist essentially of, or consist of, triphenylphosphite.

Solvent

As described above, the polythiol composition can be formed in the presence of a solvent. The solvent can comprise, consist essentially of, or consist of, a hydrocarbon, an aromatic hydrocarbon, a ketone, an alcohol, an ether, and the like, or combinations thereof. Hence, mixtures and/or combinations of solvents may be utilized in the processes of forming polythiol compositions disclosed herein.

In an embodiment, the solvent employed in forming the polythiol composition comprises, consists essentially of, or consists of, a hydrocarbon solvent. Suitable hydrocarbon solvents can include, for example, aliphatic hydrocarbons, petroleum distillates, and the like, or combinations thereof. Aliphatic hydrocarbons which may be useful as the solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons may be cyclic or acyclic and/or may be linear or branched, unless otherwise specified.

Non-limiting examples of suitable acyclic aliphatic hydrocarbon solvents that may be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, hexane (n-hexane or a mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

Non-limiting examples of suitable cyclic aliphatic hydrocarbon solvents include, but are not limited to, cyclohexane, methyl cyclohexane, and the like, or combinations thereof; alternatively cyclohexane; or alternatively, methylcyclohexane.

In an embodiment, the solvent employed in forming the polythiol composition comprises, consists essentially of, or consists of, an aromatic hydrocarbon solvent. Aromatic hydrocarbons which may be useful as a solvent include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that may be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

In an embodiment, the solvent employed in forming the polythiol composition comprises, consists essentially of, or consists of, a ketone solvent, an alcohol solvent, an ether solvent, or combinations thereof; alternatively, a ketone solvent; alternatively, an alcohol solvent; or alternatively, an ether solvent. Ketones, alcohols, or ethers which may be useful as a solvent include $C_2$ to $C_{20}$ ketones, alcohols, or ethers; alternatively, $C_2$ to $C_{10}$ ketones, alcohols, or ethers; or alternatively, $C_2$ to $C_5$ ketones, alcohols, or ethers. Non-limiting examples of suitable ketones which may be utilized as a solvent include acetone, ethyl methyl ketone, and combinations thereof. Non-limiting examples of suitable alcohols which may be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof. Suitable ether solvents may be cyclic or acyclic. Non-limiting examples of suitable ethers which may be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group.

Polythiol Compositions

Embodiments of the present invention also are directed to polythiol compositions comprising, consisting essentially of, or consisting of, sulfur-containing compounds. In some embodiments, the compositions include the polythiol composition produced by any of the processes described herein. For instance, the present invention provides a polythiol composition produced by a process comprising contacting a hydrocarbon compound having at least two olefinic double bonds, $H_2S$, and a phosphite compound; and forming the polythiol composition. In some embodiments, the molar ratio of $H_2S$ to olefinic double bond of the hydrocarbon compound can be in a range, for example, from 10:1 to 500:1, from 20:1 to 500:1, or from 40:1 to 500:1. It is contemplated that the polythiol compositions disclosed herein, which comprise (or consist essentially of, or consist of) sulfur-containing compounds, may have relatively less odor than compositions produced by other processes of producing polythiol compositions. Polythiol compositions produced by these other processes may have levels of odor which are offensive or objectionable, and in some instances, this offensive or objectionable odor may preclude the use of the polythiol composition in certain end-use applications.

Polythiol Compositions Derived from Cyclododecatriene

In embodiments of this invention, a polythiol composition derived from cyclododecatriene is provided, and this composition comprises sulfur-containing compounds. The sulfur-containing compounds of this polythiol composition can comprise:

i) an average of at least 20 wt. % thiol sulfur; and
ii) an average of from 0.1 to 8 wt. % sulfide sulfur.

In some embodiments, the sulfur-containing compounds can comprise an average of at least 22 wt. % thiol sulfur (e.g., sulfur from a —SH group); alternatively, an average of at least 25 wt. % thiol sulfur; alternatively, an average of at least 26 wt. % thiol sulfur; alternatively, an average of from 20 to 36 wt. % thiol sulfur; alternatively, an average of from 22 to 34 wt. % thiol sulfur; or alternatively, an average of from 25 to 32 wt. % thiol sulfur. Additionally, the sulfur-containing compounds can comprise an average of from 0.2 to 8 wt. % sulfide sulfur (e.g., sulfur from a —S— group); alternatively, an average of from 0.2 to 7 wt. % sulfide sulfur; alternatively, an average of from 0.3 to 6 wt. % sulfide sulfur; alternatively, an average of from 0.4 to 5 wt. % sulfide sulfur; or alternatively, an average of from 0.5 to 4 wt. % sulfide sulfur.

In another embodiment, the sulfur-containing compounds of the polythiol composition can comprise, for instance, from 30 to 80 wt. % trimercaptocyclododecane, from 35 to 70 wt. % trimercaptocyclododecane, or from 40 to 60 wt. % trimercaptocyclododecane. Additionally or alternatively, the sulfur-containing compounds can comprise from 10 to 60 wt. % dimercaptocyclododecene, such as, for example, from 20 to 55 wt. % dimercaptocyclododecene, from 25 to 55 wt. % dimercaptocyclododecene, or from 30 to 55 wt. % dimercaptocyclododecene.

In these and other embodiments, the weight ratio of trimercaptocyclododecane to dimercaptocyclododecene in the polythiol composition can fall within a range from 0.5:1 to 10:1. Accordingly, weight ratios of trimercaptocyclododecane to dimercaptocyclododecene in the polythiol composition of, for example, from 0.75:1 to 6:1, or from 0.9:1 to 2.5:1, are contemplated herein.

Typically, monomercaptocyclododecadiene is a minor component of the polythiol composition. In general, the sulfur-containing compounds of the polythiol composition comprise less than or equal to 5 wt. % monomercaptocyclododecadiene. Alternatively, the sulfur-containing compounds of the polythiol composition can comprise less than or equal to 3 wt. % monomercaptocyclododecadiene; alternatively, less than or equal to 2 wt. % monomercaptocyclododecadiene; alternatively, less than or equal to 1.5 wt. % monomercaptocyclododecadiene; alternatively, from 0.1 to 5 wt. % monomercaptocyclododecadiene; alternatively, from 0.2 to 3 wt. % monomercaptocyclododecadiene; alternatively, from 0.25 to 2 wt. % monomercaptocyclododecadiene; or alternatively, from 0.3 to 1.5 wt. % monomercaptocyclododecadiene.

Similarly, sulfide compounds can be minor components of the polythiol composition (compounds having a —S— group are sulfide compounds). In an embodiment, the sulfur-containing compounds of the polythiol composition comprise less than or equal to 30 wt. % sulfide compounds; alternatively, less than or equal to 25 wt. % sulfide compounds; alternatively, less than or equal to 20 wt. % sulfide compounds; alternatively, less than or equal to 17.5 wt. % sulfide compounds; alternatively, less than or equal to 15 wt. % sulfide compounds; or alternatively, less than or equal to 12.5 wt. % sulfide compounds. In another embodiment, the sulfur-containing compounds of the polythiol composition comprise from 3 to 20 wt. % sulfide compounds; alternatively, from 4 to 17.5 wt. % sulfide compounds; alternatively, from 5 to 15 wt. % sulfide compounds; or alternatively, from 6 to 12.5 wt. % sulfide compounds.

These sulfide compounds can be further characterized as being intermolecular sulfide compounds (e.g., compounds where two cyclic rings derived from cyclododecatriene are connected by a —S— group; thiol groups can be present on the rings) or intramolecular sulfide compounds (e.g., compounds where the —S— group connects two carbon atoms of a single cyclododecatriene ring; a thiol group can be present on the ring). In some embodiments, the weight ratio of intermolecular sulfide compounds to intramolecular sulfide compounds in the polythiol composition can be in a range from 0.1:1 to 15:1; alternatively, in a range from 0.1:1 to 10:1; or alternatively, in a range from 0.1:1 to 5:1.

In some embodiments, the weight ratio of trimercaptocyclododecane to intramolecular sulfide compounds in the polythiol composition can be at least 3:1 or at least 4:1. For instance, weight ratios of trimercaptocyclododecane to intramolecular sulfide compounds in the polythiol composition can be from 3:1 to 40:1, from 3:1 to 30:1, from 3:1 to 20:1, from 4:1 to 20:1, or from 4:1 to 18:1.

The polythiol composition derived from cyclododecatriene generally contains very little, if any, cyclododecatriene. In one embodiment, the polythiol composition comprises less than 5 wt. % cyclododecatriene, while in another embodiment, the polythiol composition comprises less than 2.5 wt. % cyclododecatriene. In yet another embodiment, the composition comprises less than 1 wt. % cyclododecatriene or, alternatively, less than 0.5 wt. % cyclododecatriene.

Polythiol Compositions Derived from Trivinylcyclohexane

In embodiments of this invention, a polythiol composition derived from trivinylcyclohexane is provided, and this composition comprises sulfur-containing compounds. The sulfur-containing compounds of this polythiol composition can comprise:

i) an average of at least 20 wt. % thiol sulfur; and
ii) an average of from 0.1 to 8 wt. % sulfide sulfur.

In some embodiments, the sulfur-containing compounds can comprise an average of at least 22 wt. % thiol sulfur; alternatively, an average of at least 25 wt. % thiol sulfur; alternatively, an average of from 20 to 36 wt. % thiol sulfur; alternatively, an average of from 22 to 34 wt. % thiol sulfur; or alternatively, an average of from 25 to 32 wt. % thiol sulfur. Additionally, the sulfur-containing compounds can comprise an average of from 0.2 to 8 wt. % sulfide sulfur (e.g., sulfur from a —S— group); alternatively, an average of from 0.2 to 7 wt. % sulfide sulfur; alternatively, an average of from 0.3 to 6 wt. % sulfide sulfur; alternatively, an average of from 0.4 to 5 wt. % sulfide sulfur; or alternatively, an average of from 0.5 to 4 wt. % sulfide sulfur.

In another embodiment, the sulfur-containing compounds of the polythiol composition can comprise, for instance, from 30 to 85 wt. % tri(2-mercaptoethyl)cyclohexane, from 35 to 80 wt. % tri(2-mercaptoethyl)cyclohexane, or from 40 to 75 wt. % tri(2-mercaptoethyl)cyclohexane. Additionally or alternatively, the sulfur-containing compounds can comprise from 0 to 50 wt. % di(2-mercapto-ethyl)vinylcyclohexane, such as, for example, from 0 to 45 wt. % di(2-mercaptoethyl)-vinylcyclohexane, from 0 to 40 wt. % di(2-mercaptoethyl) vinylcyclohexane, or from 0 to 35 wt. % di(2-mercaptoethyl) vinylcyclohexane. In another embodiment, the sulfur-containing compounds can comprise from 10 to 60 wt. % di(2-mercaptoethyl)vinylcyclohexane, such as, for example, from 20 to 55% wt. % di(2-mercaptoethyl)vinylcyclohexane, from 25 to 55 wt. % di(2-mercaptoethyl)vinylcyclohexane, or from 30 to 55 wt. % di(2-mercaptoethyl)-vinylcyclohexane. Yet, in another embodiment, the sulfur-containing compounds can comprise less than 15 wt. % di(2-mercaptoethyl) vinylcyclohexane; alternatively, less than 10 wt. %; alternatively, in a range from 0.1 to 10 wt. %; or alternatively, in a range from 0.1 to 8 wt. %.

In these and other embodiments, the weight ratio of tri(2-mercaptoethyl)cyclohexane to di(2-mercaptoethyl)vinylcyclohexane in the polythiol composition can be greater than or equal to 2:1. Accordingly, weight ratios of tri(2-mercaptoethyl)cyclohexane to di(2-mercaptoethyl)vinylcyclohexane in the polythiol composition, for example, of greater than or equal to 4:1, of greater than or equal to 6:1, in a range from 2:1 to 60:1, in a range from 4:1 to 20:1, or in a range from 6:1 to 15:1, are contemplated herein.

Typically, (2-mercaptoethyl)divinylcyclohexane is a minor component of the polythiol composition. In general, the sulfur-containing compounds of the polythiol composition comprise less than or equal to 5 wt. % (2-mercaptoethyl) divinylcyclohexane. Alternatively, the sulfur-containing compounds of the polythiol composition can comprise less than or equal to 3 wt. % (2-mercaptoethyl)divinylcyclohexane; alternatively, less than or equal to 2 wt. % (2-mercaptoethyl)divinylcyclohexane; alternatively, less than or equal to 1 wt. % (2-mercaptoethyl)divinylcyclohexane; alternatively, less than or equal to 0.5 wt. % (2-mercaptoethyl)divinylcyclohexane; or alternatively, less than or equal to 0.25 wt. % (2-mercaptoethyl)divinylcyclohexane.

In an embodiment, the sulfur-containing compounds of the polythiol composition comprise from 10 to 50 wt. % sulfide compounds; alternatively, from 12 to 45 wt. % sulfide compounds; alternatively, from 15 to 45 wt. % sulfide compounds; or alternatively, from 15 to 40 wt. % sulfide compounds.

These sulfide compounds can be further characterized as being intermolecular sulfide compounds or intramolecular sulfide compounds. In some embodiments, the weight ratio of intermolecular sulfide compounds to intramolecular sulfide compounds in the polythiol composition can be in a range from 1:1 to 30:1; alternatively, in a range from 1:1 to 20:1; or alternatively, in a range from 2:1 to 10:1.

The polythiol composition derived from trivinylcyclohexane generally contains very little, if any, trivinylcyclohexane. In one embodiment, the polythiol composition comprises less than 10 wt. % trivinylcyclohexane, while in another embodiment, the polythiol composition comprises less than 5 wt. % trivinylcyclohexane. In yet another embodiment, the composition comprises less than 3 wt. % trivinylcyclohexane; alternatively, less than 2 wt. % trivinylcyclohexane; alternatively, less than 1 wt. % trivinylcyclohexane; alternatively, less than 0.5 wt. % trivinylcyclohexane; or alternatively, less than 0.25 wt. % trivinylcyclohexane.

Polythiol Compositions Derived from Cyclooctadiene

In embodiments of this invention, a polythiol composition derived from cyclooctadiene is provided, and this composition comprises sulfur-containing compounds. The sulfur-containing compounds of this polythiol composition can comprise:

i) an average of at least 22 wt. % thiol sulfur; and
ii) an average of from 0.1 to 5 wt. % sulfide sulfur.

In some embodiments, the sulfur-containing compounds can comprise an average of at least 25 wt. % thiol sulfur; alternatively, an average of at least 28 wt. % thiol sulfur; alternatively, an average of from 22 to 36 wt. % thiol sulfur;

alternatively, an average of from 25 to 35 wt. % thiol sulfur; or alternatively, an average of from 28 to 34 wt. % thiol sulfur. Additionally, the sulfur-containing compounds can comprise an average of from 0.1 to 4 wt. % sulfide sulfur; alternatively, an average of from 0.2 to 4 wt. % sulfide sulfur; or alternatively, an average of from 0.2 to 3 wt. % sulfide sulfur.

In another embodiment, the sulfur-containing compounds of the polythiol composition can comprise, for instance, at least 50 wt. % dimercaptocyclooctane, at least 55 wt. % dimercaptocyclooctane, at least 60 wt. % dimercaptocyclooctane, at least 65 wt. % dimercaptocyclooctane, at least 70 wt. % dimercaptocyclooctane, at least 75 wt. % dimercaptocyclooctane, from 60 to 99 wt. % dimercaptocyclooctane, from 65 to 95 wt. % dimercaptocyclooctane, or from 75 to 92 wt. % dimercaptocyclooctane.

Sulfide compounds can be minor components of the polythiol composition. In an embodiment, the sulfur-containing compounds of the polythiol composition comprise from 2 to 45 wt. % sulfide compounds, such as, for example, from 3 to 40 wt. % sulfide compounds; alternatively, from 4 to 35 wt. % sulfide compounds; or alternatively, from 5 to 30 wt. % sulfide compounds.

In these and other embodiments, the weight ratio of dimercaptocyclooctane to intermolecular sulfide compounds in the polythiol composition can fall within a range from 1:1 to 25:1, from 1.5:1 to 20:1, or from 2:1 to 15:1. Yet, in another embodiment, the weight ratio of dimercaptocyclooctane to intermolecular sulfide compounds in the polythiol composition can be in a range from 10:1 to 25:1; alternatively, from 13:1 to 22:1; or alternatively, from 15:1 to 20:1. Additionally, weight ratios of dimercaptocyclooctane to intermolecular sulfide compounds in the polythiol composition of, for example, from 1:1 to 10:1, from 1.5: to 9:1, or from 2:1 to 8:1, are contemplated herein.

Typically, monomercaptocyclooctene and thiabicyclononane are minor components of the polythiol composition. In general, the sulfur-containing compounds of the polythiol composition comprise a total monomercaptocyclooctene and thiabicyclononane content of less than 5 wt. %. Alternatively, the sulfur-containing compounds of the polythiol composition can comprise a total monomercaptocyclooctene and thiabicyclononane content of less than 4 wt. %; alternatively, less than 3 wt. %; alternatively, less than 2 wt. %; alternatively, less than 1 wt. %; or alternatively, less than 0.5 wt. %.

The polythiol composition derived from cyclooctadiene generally contains very little, if any, cyclooctadiene. In one embodiment, the polythiol composition comprises less than 5 wt. % cyclooctadiene, while in another embodiment, the polythiol composition comprises less than 3 wt. % cyclooctadiene. In yet another embodiment, the composition comprises less than 2 wt. % cyclooctadiene; alternatively, less than 1% wt. % cyclooctadiene; alternatively, less than 0.5 wt. % cyclooctadiene; or alternatively, less than 0.25 wt. % cyclooctadiene.

Articles

The polythiol compositions disclosed herein can be used as curing agents for epoxy and urethane adhesives and other articles. For instance, the adhesives and other articles can be used with, or can contain, metal (e.g., aluminum, steel, copper, etc.), wood, glass, ceramic, and plastic substrates, including combinations of these substrates.

Formulations containing the polythiol compositions can contain other additives or components depending upon the desired properties and end-use application. These additives or components can include, but are not limited to, catalysts, solvents/diluents, plasticizers, fillers, fibers, pigments/colorants, pigment dispersing agents, flow modifiers, surface modifiers, antioxidants or stabilizers, or combinations thereof.

It is contemplated that formulations, adhesives, and other articles that contain and/or are produced from the polythiol compositions disclosed herein may have lower levels of offensive or objectionable odor, as compared to compositions produced by other processes of producing polythiol compositions.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The polythiol compositions of Examples 1 to 44 were produced in accordance with the following procedure. Either a 1.5-L or a 5-L ultraviolet light reactor was used for each example; working volumes were 1.2 L and 4 L, respectively. Each stainless-steel reactor had a quartz lamp well mounted horizontal to an off-set stir shaft. The reactors were equipped with a thermowell, cooling coils, a charge port, a sample port, and a bottom drain valve. To the respective reactor, the hydrocarbon compound (e.g., cyclododecatriene, trivinylcyclohexane, etc.), the desired amount of phosphite compound, free radical initiator (if utilized), photoinitiator (if utilized), and solvent (if utilized) were charged to the reactor through the charge port. The reactor was sealed and pressure checked with nitrogen at 450 psig. The reactor was vented and the desired amount of $H_2S$ was charged to the reactor. The reactor contents were heated and controlled by setting the external circulating bath at the desired temperature (e.g., about 35° C. for UV-initiated Examples 1 to 44).

The reaction mixture was allowed to mix for up to about 1 hour (this could be much less or much more than 1 hour). After this mixing period, the ultraviolet lamp was turned on, and the progress of the thiolation reaction was monitored for some of the runs. The ultraviolet lamp typically required 3-5 minutes to reach full power. The ultraviolet lamp power was 100-200 watts, and the photon rate at 320 nm and below was about $6.6 \times 10^{-6}$ to $1.46 \times 10^{-5}$ einsteins/sec.

When the conversion of olefinic double bonds was complete or was no longer changing, the lamp was turned off. The $H_2S$ was slowly vented from the reactor. Then, the reactor was purged with nitrogen and the contents were drained via a bottom drain valve. In some cases, the crude product was then placed in a rotoevaporator at 60° C. and low vacuum to remove additional residual $H_2S$ and other light materials (e.g., solvent). This stripped product was then analyzed using Gas Chromatography (GC). GC analysis of the sulfur-containing compounds excluded peaks attributed to phosphorus-containing materials. Product composition information based upon GC data in Tables I-VII that follow is presented in area percentages, unless otherwise specified.

In some examples, a wiped film evaporator was utilized. The wiped film evaporator was run under standard operating procedures, with a wall temperature of the vessel (glass) in the 100-140° C. range, and pressure in the 1-2 torr range. The wiper blades typically operated at 200-300 rpm. The rate of addition of the incoming product was in the 50-300 cc/hr range. Operating conditions varied depending on the volatility of the material(s) to be removed, among other factors.

Examples 1-23

Polythiol Compositions Produced from Cyclododecatriene

Examples 1-23 utilized the general experimental procedure described above. The temperature was in the 35-45° C. range, and the pressure was in the 400-450 psig range. Table I summarizes certain process conditions and analytical results of the polythiol compositions of Examples 1-23. The analytical results were determined via gas chromatography. The following abbreviations and conventions are used in Table I: Weight CDDT=Weight of cyclododecatriene; TEP=triethylphosphite; TBP=tributylphosphite; Phosphite Weight Percentage=(weight of phosphite compound/weight of cyclododecatriene)×100; Phosphite Molar Ratio=moles of phosphite compound/moles of olefinic double bond of cyclododecatriene (i.e., moles of phosphite compound/moles of olefin equivalents of cyclododecatriene); $H_2S$ Molar Ratio=Moles of $H_2S$/moles of olefinic double bond of cyclododecatriene; Irg184=Irgacure® 184; Irg500=Irgacure® 500; AIBN=α,α'-azo diisobutyronitrile; Dual=60/40 mixture of Irgacure® 819 and Darocur 1173; Additive Weight Percentage=(weight of additive/weight of cyclododecatriene)×100; CDDT=unreacted cyclododecatriene; monoSH=monomercaptocyclododecadiene; monoS-mono-ene=cyclic intramolecular sulfide compounds; Total monoS=total amount having one sulfur; diSH=dimercaptocyclododecene; SH-cyclicS=monothiol intramolecular sulfide compounds; diS total=total amount having two sulfurs; triSH=trimercaptocyclododecane; and sulfide dimer=thiol-containing intermolecular sulfide compounds.

Examples 1-2 (among others) illustrate the impact of using no phosphite at two ratios of $H_2S$/olefin. Examples 2-3 (among others) illustrate the impact of phosphite addition on conversion and triSH. Examples 5-6 (among others) illustrate differences between the two reactors under similar process conditions. Examples 3 and 21 (among others) illustrate the impact of AIBN addition on reaction time and cyclic sulfide content. Example 23 is a Comparative Example, illustrating the low conversion and low production of triSH resulting from the $H_2S$/olefin ratio of 1.1; the major product produced was monomercaptocyclododecadiene.

TABLE I

| Thiolation of Cyclododecatriene - Examples 1-23. | | | | | | | | | | |
|---|---|---|---|---|---|---|---|---|---|---|
| Example | Reactor | Weight. CDDT (g) | Weight $H_2S$ (g) | Phosphite Compound | Phosphite Weight Percentage | Phosphite Molar Ratio | $H_2S$ Molar Ratio | Other additive | Additive Weight Percentage | Reaction Time (min) | % Conversion |
| 1 | 5-L | 430 | 2700 | none | 0 | 0 | 10 | | | 132 | 38 |
| 2 | 5-L | 43 | 2700 | none | 0 | 0 | 100 | | | 120 | 28 |
| 3 | 5-L | 43 | 2700 | TEP | 9.09 | 0.033 | 100 | | | 100 | 76 |
| 4 | 5-L | 43 | 3000 | TBP | 24.56 | 0.070 | 111 | | | 80 | 77 |
| 5 | 5-L | 43 | 2700 | TBP | 13.13 | 0.033 | 100 | | | 60 | 70 |
| 6 | 1.5-L | 13 | 900 | TBP | 13.13 | 0.033 | 110 | | | 60 | 73 |
| 7 | 5-L | 20 | 3100 | TEP | 25.37 | 0.073 | 246 | | | 49 | 78 |
| 8 | 1.5-L | 47 | 900 | TBP | 0.21 | 0.001 | 30 | | | 105 | 44 |
| 9 | 1.5-L | 15 | 900 | TBP | 5.06 | 0.012 | 95 | | | 96 | 62 |
| 10 | 1.5-L | 24 | 900 | TBP | 1.64 | 0.004 | 60 | | | 96 | 55 |
| 11 | 1.5-L | 24 | 900 | none | 0 | 0 | 60 | Irg184 | 5.0 | 60 | 37 |
| 12 | 1.5-L | 24 | 900 | TBP | 4.76 | 0.011 | 60 | Irg500 | 5.0 | 45 | 70 |
| 13 | 1.5-L | 24 | 900 | TBP | 11.44 | 0.028 | 50 | Dual | 1.7 | 60 | 77 |
| 14 | 5-L | 96 | 3000 | TBP | 13.20 | 0.033 | 50 | Dual | 2.1 | 120 | |
| 15 | 5-L | 158 | 3000 | TEP | 7.06 | 0.025 | 30 | Irg500 | 0.2 | 60 | 64 |
| 16 | 5-L | 158 | 3000 | TEP | 13.19 | 0.049 | 30 | Irg500 | 0.3 | 66 | 76 |
| 17 | 5-L | 158 | 3000 | TEP | 13.19 | 0.049 | 30 | Irg500 | 0.3 | 60 | 72 |
| 18 | 5-L | 43 | 2700 | TEP | 13.13 | 0.033 | 100 | Acetone | 100.0 | 56 | 68 |
| 19 | 5-L | 158 | 3000 | TEP | 7.06 | 0.016 | 30 | AIBN | 0.6 | 60 | 66 |
| 20 | 5-L | 158 | 3000 | TEP | 7.06 | 0.016 | 30 | AIBN | 1.9 | 13 | 77 |
| 21 | 5-L | 43 | 3000 | TEP | 9.09 | 0.022 | 111 | AIBN | 2.3 | 13 | 76 |
| 23 | 5-L | 1900 | 1350 | TEP | 2.41 | 0.005 | 1.1 | | | 90 | 24 |

| Example | % CDDT | % monoSH | % monoS - mono-ene | % Total monoS | % diSH | % SH-cyclicS | % diS total | % triSH | % sulfide dimer | triSH/diSH Ratio |
|---|---|---|---|---|---|---|---|---|---|---|
| 1 | 23.16 | 65.94 | 0.45 | 66.39 | 7.94 | 0.58 | 8.52 | 1.20 | 0.74 | 0.15 |
| 2 | 9.95 | 71.56 | 0.36 | 71.92 | 16.16 | 1.01 | 17.17 | 1.27 | 0.10 | 0.08 |
| 3 | 0.94 | 9.56 | 0.53 | 10.09 | 37.76 | 9.11 | 46.86 | 42.08 | 0.03 | 1.11 |
| 4 | 0.94 | | | 10.15 | 36.68 | 9.35 | 46.03 | 42.88 | 0.00 | 1.17 |
| 5 | 0.93 | 8.55 | 0.63 | 9.18 | 35.32 | 8.96 | 44.28 | 45.09 | 0.52 | 1.28 |
| 6 | 3.55 | 21.50 | 0.50 | 22.00 | 41.99 | 6.48 | 48.47 | 25.99 | 0.00 | 0.62 |
| 7 | 1.73 | 8.52 | 1.32 | 9.84 | 38.61 | 9.49 | 48.10 | 40.33 | 0.00 | 1.04 |
| 8 | 4.25 | | | 64.60 | 26.00 | 1.01 | 27.01 | 3.54 | 0.60 | 0.14 |
| 9 | 3.76 | | | 32.26 | 40.87 | 5.38 | 46.25 | 17.43 | 3.53 | 0.43 |
| 10 | 3.32 | 47.66 | 0.37 | 48.03 | 35.24 | 3.79 | 39.03 | 9.09 | 0.54 | 0.26 |
| 11 | 9.33 | 70.85 | 0.35 | 71.20 | 17.25 | 0.95 | 18.19 | 1.28 | 0.00 | 0.07 |
| 12 | 2.63 | 21.45 | 2.35 | 23.80 | 40.99 | 6.54 | 47.52 | 24.59 | 0.25 | 0.60 |
| 13 | 2.06 | 14.07 | 1.24 | 15.31 | 42.49 | 6.36 | 48.85 | 33.71 | 0.07 | 0.79 |
| 14 | 0.85 | 9.54 | 0.40 | 9.95 | 40.93 | 6.52 | 47.44 | 47.44 | 0.00 | 1.16 |
| 15 | 0.21 | 23.28 | 0.87 | 24.15 | 45.84 | 5.25 | 51.09 | 24.55 | 0.00 | 0.54 |
| 16 | 0.14 | 14.80 | 1.07 | 15.87 | 44.57 | 5.87 | 50.44 | 33.56 | 0.00 | 0.75 |
| 17 | 0.14 | 12.64 | 1.10 | 13.74 | 44.24 | 6.45 | 50.69 | 35.44 | 0.00 | 0.80 |

TABLE I-continued

Thiolation of Cyclododecatriene - Examples 1-23.

| | | | | | | | | | |
|---|---|---|---|---|---|---|---|---|---|
| 18 | 0.56 | 14.77 | 0.90 | 15.68 | 40.06 | 8.59 | 48.66 | 35.09 | 0.00 | 0.88 |
| 19 | 0.31 | 12.86 | 1.05 | 13.91 | 40.24 | 9.45 | 49.69 | 34.75 | 1.34 | 0.86 |
| 20 | 0.25 | | | 19.53 | 34.18 | 13.90 | 48.08 | 27.31 | 4.83 | 0.80 |
| 21 | 0.93 | 10.91 | 2.14 | 13.05 | 33.40 | 12.44 | 45.85 | 38.73 | 1.44 | 1.16 |
| 23 | 12.63 | 66.71 | 2.37 | 69.07 | 10.49 | 2.07 | 12.51 | 0.61 | 5.11 | 0.06 |

Examples 24-33

Polythiol Compositions Produced from Cyclooctadiene

Examples 24-33 utilized the general experimental procedure described above. The temperature was in the 35-45° C. range, and the pressure was in the 400-450 psig range. Table II summarizes certain process conditions and analytical results of the polythiol compositions of Examples 24-33. The analytical results were determined via gas chromatography. The following abbreviations and conventions are used in Table II: Weight COD=Weight of cyclooctadiene; TEP=triethylphosphite; TBP=tributylphosphite; Phosphite Weight Percentage=(weight of phosphite compound/weight of cyclooctadiene)×100; Phosphite Molar Ratio=moles of phosphite compound/moles of olefinic double bond of cyclooctadiene; $H_2S$ Molar Ratio=Moles of $H_2S$/moles of olefinic double bond of cyclooctadiene; Additive Weight Percentage=(weight of additive/weight of cyclooctadiene)×100; COD=unreacted cyclooctadiene; cyclic Sulfide=intramolecular sulfide compounds; other monoSH=monomercaptocyclooctene and monomercaptocyclooctane; total monoS=total amount having one sulfur; diSH=dimercaptocyclooctane; and Heavies=thiol-containing intermolecular sulfide compounds.

Examples 24 and 31 (among others) illustrate the impact of phosphite on reaction time and conversion. Examples 24 and 33 illustrate the impact of AIBN addition in the absence of the phosphite. Examples 24 and 31-33 (among others) illustrate the impact of AIBN and TEP on reaction time and conversion, as well as on the amount of sulfides produced. Note the conversions of 99% for Examples 31-32. Examples 25-27 illustrate the impact of the $H_2S$ ratio and phosphite ratio. Examples 28-30 illustrate the experimental reproducibility.

TABLE II

Thiolation of Cyclooctadiene - Examples 24-33.

| Example# | Reactor | Weight COD (g) | Weight $H_2S$ (g) | Phosphite Compound | Phosphite Weight Percentage | Phosphite Molar Ratio | $H_2S$ Molar Ratio | Other additive | Additive Weight Percentage | Reaction Time (min) | % Conversion |
|---|---|---|---|---|---|---|---|---|---|---|---|
| 24 | 5-L | 158 | 3000 | none | 0 | 0 | 30 | | | 90 | 59 |
| 25 | 1.5-L | 13 | 900 | TBP | 15.38 | 0.008 | 100 | | | 50 | 97 |
| 26 | 1.5-L | 45 | 900 | TBP | 4.44 | 0.008 | 30 | | | 60 | 99 |
| 27 | 1.5-L | 13 | 900 | TBP | 30.70 | 0.016 | 100 | | | 15 | 98 |
| 28 | 5-L | 96 | 3000 | TBP | 7.20 | 0.028 | 50 | | | 30 | 98 |
| 29 | 5-L | 96 | 3000 | TEP | 7.20 | 0.023 | 50 | | | 50 | 100 |
| 30 | 5-L | 96 | 3000 | TEP | 7.20 | 0.023 | 50 | | | 45 | 100 |
| 31 | 5-L | 158 | 3000 | TEP | 7.59 | 0.025 | 30 | | | 60 | 99 |
| 32 | 5-L | 158 | 3000 | TEP | 7.59 | 0.025 | 30 | AIBN | 0.6 | 20 | 99 |
| 33 | 5-L | 158 | 3000 | none | 0 | 0 | 30 | AIBN | 0.6 | 60 | 63 |

| Example | % COD | % cyclic Sulfide | % other monoSH | Total % monoS | % diSH | % Heavies | Ratio diSH/ Total monoS | Ratio diSH/ cyclic Sulfide | Ratio diSH/ Heavies |
|---|---|---|---|---|---|---|---|---|---|
| 24 | 0.43 | 7.98 | 56.46 | 64.43 | 25.13 | 7.61 | 0.39 | 3.15 | 3.30 |
| 25 | 5.55 | 5.24 | 4.38 | 9.62 | 74.34 | 4.24 | 7.73 | 14.19 | 17.53 |
| 26 | 4.82 | 8.80 | 7.36 | 16.17 | 61.38 | 9.49 | 3.80 | 6.97 | 6.47 |
| 27 | 0.67 | 5.51 | 11.22 | 16.72 | 73.79 | 4.12 | 4.41 | 13.40 | 17.89 |
| 28 | 0.33 | 9.02 | 5.47 | 14.49 | 73.76 | 8.48 | 5.09 | 8.18 | 8.70 |
| 29 | 0.37 | 8.15 | 6.67 | 14.82 | 74.18 | 8.23 | 5.01 | 9.10 | 9.01 |
| 30 | 0.40 | 9.22 | 6.15 | 15.37 | 73.25 | 8.81 | 4.77 | 7.94 | 8.32 |
| 31 | 0.26 | 9.76 | 6.52 | 16.28 | 69.34 | 10.47 | 4.26 | 7.11 | 6.62 |
| 32 | 0.19 | 10.49 | 7.01 | 17.50 | 67.31 | 10.72 | 3.85 | 6.42 | 6.28 |
| 33 | 0.27 | 9.55 | 53.30 | 62.85 | 26.19 | 8.90 | 0.42 | 2.74 | 2.94 |

Examples 34-44

Polythiol Compositions Produced from Trivinylcyclohexane

Examples 34-44 utilized the general experimental procedure described above. The temperature was in the 35-45° C. range, and the pressure was in the 400-450 psig range. Table III summarizes certain process conditions and analytical results of the polythiol compositions of Examples 34-44. The analytical results were determined via gas chromatography. The following abbreviations and conventions are used in Table III: Weight TVCH=Weight of trivinylcyclohexane; TBP=tributylphosphite; Phosphite Weight Percentage= (weight of phosphite compound/weight of trivinylcyclohexane)×100; Phosphite Molar Ratio=moles of phosphite compound/moles of olefinic double bond of trivinylcyclohexane;

$H_2S$ Molar Ratio=Moles of $H_2S$ moles of olefinic double bond of trivinylcyclohexane; Irg500=Irgacure® 500; Additive Weight Percentage=(weight of additive/weight of trivinylcyclohexane)×100; SH=% mercaptan sulfur by iodine titration; TVCH=unreacted trivinylcyclohexane; monoSH=total amount having one sulfur; diSH=di(2-mercaptoethyl)vinylcyclohexane; SH-cyclicS=monothiol intramolecular sulfide compounds; triSH=tri(2-mercaptoethyl)cyclohexene; and sulfide dimer=thiol-containing intermolecular sulfide compounds.

Examples 34 and 44 (among others) illustrate the impact of the absence of a phosphite compound on conversion, and the impact of $H_2S$ ratio on triSH. Example 40 (among others) illustrates the impact of the photoinitiator on triSH. Examples 34 and 41-43 (among others) illustrate the impacts of the phosphite ratio and the $H_2S$ ratio on conversion and triSH. Examples 38-39 illustrate the impact of the addition of a photoinitiator, resulting in a faster reaction and increased triSH. Example 44 is a Comparative Example, illustrating the low conversion and low production of triSH resulting from the $H_2S$/olefin ratio of 5.3 with no phosphite; the major products produced were monoSH.

after 125 min, the temperature was increased to 90° C. For Example 47, after 1 hour, the temperature was increased to 90° C. and reached 90° C. after about 90 min Samples were taken at about 60 min after heating, because sample analysis indicated high conversion. For Example 48, after 1 hour, the temperature was increased to 45° C. and held at that temperature. For Examples 49-50, after 30 min, the temperature was increased to and reached 70° C. after 60 min; the temperature was then held at 70° C. The reactor pressures for Examples 45-50 were in the 400-1100 psig range (e.g., the pressure at 45° C. in Example 48 was about 450 psig, while the pressure at 90° C. in Example 47 was in the 1000-1100 psig range).

Table IV summarizes certain process conditions and analytical results of the polythiol compositions of Examples 45-50. The analytical results were determined via gas chromatography. The following abbreviations and conventions are used in Table IV: TBP=tributylphosphite; Phosphite Weight Percentage=(weight of phosphite compound/weight of cyclooctadiene)×100; $H_2S$ Molar Ratio=Moles of $H_2S$ moles of olefinic double bond of cyclooctadiene; AIBN Weight Percentage=(weight of AIBN/weight of cyclooctadi-

TABLE III

Thiolation of Trivinylcyclohexane - Examples 34-44.

| Example | Reactor | Weight TVCH (g) | Weight $H_2S$ (g) | Phosphite Compound | Phosphite Weight Percentage | Phosphite Molar Ratio | $H_2S$ Molar Ratio | Other additive | Additive Weight Percentage | Reaction Time (min) | % Conversion |
|---|---|---|---|---|---|---|---|---|---|---|---|
| 34 | 1.5-L | 42 | 880 | none | 0 | 0 | 33 | | | 120 | 46.0 |
| 35 | 1.5-L | 42 | 880 | TBP | 7.17 | 0.016 | 33 | | | 120 | 80.4 |
| 36 | 1.5-L | 42 | 880 | TBP | 11.96 | 0.026 | 33 | | | 60 | 96.7 |
| 37 | 1.5-L | 42 | 880 | TBP | 11.96 | 0.026 | 33 | | | 120 | 97.6 |
| 38 | 5-L | 157 | 3000 | TBP | 3.19 | 0.007 | 30 | | | 160 | 86.0 |
| 39 | 5-L | 157 | 3000 | TBP | 3.19 | 0.007 | 30 | Irg 500 | 0.2 | 120 | 98.0 |
| 40 | 5-L | 157 | 3000 | none | 0 | 0 | 30 | Irg 500 | 0.2 | 160 | 79.0 |
| 41 | 1.5-L | 42 | 880 | none | 0 | 0 | 100 | | | 120 | 55.6 |
| 42 | 1.5-L | 42 | 880 | TBP | 5.50 | 0.012 | 100 | | | 120 | 82.0 |
| 43 | 1.5-L | 42 | 880 | TBP | 11.96 | 0.026 | 100 | | | 120 | 97.3 |
| 44 | 5-L | 730 | 2450 | none | 0 | 0 | 5.3 | | | 120 | 31 |

| Example | % SH | % TVCH | % monoSH | % diSH | % SH-cyclicS | % triSH | % sulfide dimer | Ratio triSH/diSH | Ratio triSH/SH-cyclicS | Ratio triSH/monoSH |
|---|---|---|---|---|---|---|---|---|---|---|
| 34 | 23.5 | 13.51 | 36.31 | 39.83 | 0.70 | 8.81 | 0.84 | 0.22 | 12.58 | 0.24 |
| 35 | 28.3 | 1.41 | 5.23 | 37.42 | 3.48 | 41.57 | 10.90 | 1.11 | 11.95 | 7.95 |
| 36 | 27.4 | 0.10 | 0.29 | 5.07 | 5.53 | 65.40 | 23.62 | 12.91 | 11.83 | 223.98 |
| 37 | 28.7 | 0.94 | 0.37 | 1.93 | 5.47 | 69.83 | 21.47 | 36.22 | 12.76 | 191.32 |
| 38 | 28.5 | 0.84 | 5.66 | 39.59 | 3.26 | 40.47 | 10.22 | 1.02 | 12.43 | 7.15 |
| 39 | 29.6 | 0.53 | 0.92 | 16.59 | 5.24 | 57.63 | 19.08 | 3.47 | 11.00 | 62.64 |
| 40 | 27.0 | 2.45 | 17.23 | 49.09 | 2.09 | 23.43 | 5.55 | 0.48 | 11.20 | 1.36 |
| 41 | 25.0 | 6.41 | 27.95 | 47.57 | 1.26 | 16.81 | 0.00 | 0.35 | 13.36 | 0.60 |
| 42 | 27.9 | 1.97 | 7.41 | 40.55 | 3.23 | 42.29 | 4.53 | 1.04 | 13.09 | 5.71 |
| 43 | 27.7 | 1.44 | 0.59 | 2.75 | 5.83 | 70.18 | 19.14 | 25.49 | 12.03 | 118.75 |
| 44 | 16.4 | 31.4 | 42.6 | 16.6 | 2.1 | 1.5 | 5.3 | 0.09 | 0.71 | 0.04 |

Examples 45-50

Polythiol Compositions Produced from Cyclooctadiene in the Presence of AIBN and Heat Examples 45-50 utilized the general experimental procedure described above, except that ultraviolet lamps were not used and the reactions were conducted in a 1-L autoclave reactor under the following conditions: Example 45 was held at 60° C. for 1 hour; after 95 min total, the temperature was increased to 70° C.; after 240 min total, the temperature was increased to 80° C. For Example 46, after 60 min, the temperature was increased to and reached 60° C. after 80 min;

ene)×100; COD=unreacted cyclooctadiene; monoSH=monomercaptocyclooctene and monomercaptocyclooctane; cyclic Sulfide=intramolecular sulfide compounds; total monoS=total amount having one sulfur; diSH=dimercaptocyclooctane; and Heavies=thiol-containing intermolecular sulfide compounds.

These examples generally demonstrate that higher temperatures were beneficial to obtain higher olefin conversion. Interestingly, Example 48, conducted at low temperature, resulted in increased cyclic sulfide and intermolecular sulfide production. Examples 49 and 50 (among others) illustrate the impact of the presence of a phosphite compound on diSH.

TABLE IV

Thiolation of Cyclooctadiene in the presence of AIBN - Examples 45-50.

| Example | Weight COD (g) | Weight $H_2S$ (g) | Phosphite Compound | Phosphite Weight Percentage | $H_2S$ Molar Ratio | AIBN Weight Percentage | Reaction Time (min) | % Conversion |
|---|---|---|---|---|---|---|---|---|
| 45 | 12 | 375 | TBP | 0.78 | 50 | 0.78 | 300 | 76 |
| 46 | 12 | 375 | TBP | 4.1 | 50 | 4.1 | 180 | 97 |
| 47 | 12 | 375 | TBP | 4.1 | 50 | 4.1 | 120 | 99 |
| 48 | 12 | 375 | TEP | 4.1 | 50 | 4.1 | 240 | 56 |
| 49 | 14.6 | 448 | TEP | 3.8 | 50 | 3.8 | 170 | 98 |
| 50 | 14.6 | 448 | none | 0 | 50 | 3.8 | 170 | 64 |

| Example | % COD | % monoSH | % cyclic Sulfide | Total % monoS | % diSH | % Heavies | Ratio diSH/ Total monoS | Ratio diSH/ cyclic Sulfide | Ratio diSH/ Heavies |
|---|---|---|---|---|---|---|---|---|---|
| 45 | 4.15 | 31.11 | 17.33 | 48.44 | 37.69 | 8.28 | 0.78 | 2.17 | 4.55 |
| 46 | 6.67 | 4.82 | 12.83 | 17.65 | 69.36 | 5.91 | 3.93 | 5.41 | 11.74 |
| 47 | 3.20 | 3.92 | 9.38 | 13.30 | 74.92 | 7.88 | 5.63 | 7.99 | 9.51 |
| 48 | 4.76 | 44.57 | 17.97 | 62.54 | 11.30 | 19.75 | 0.18 | 0.63 | 0.57 |
| 49 | 3.42 | 2.31 | 14.65 | 16.96 | 58.05 | 21.58 | 3.42 | 3.96 | 2.69 |
| 50 | 8.04 | 66.89 | 7.28 | 74.17 | 14.28 | 3.52 | 0.19 | 1.96 | 4.05 |

Example 51

Polythiol Composition Produced from Cyclododecatriene in the Presence of AIBN and Heat Example 51 utilized the general experimental procedure described above, except that ultraviolet lamps were not used and the reaction was conducted in a 1-L autoclave reactor under the following conditions: after 1 hour, the temperature was increased to 90° C. and reached 90° C. after 80 min, at which time the reaction appeared complete. The reactor pressure was in the 900-1000 psig range.

Table V summarizes certain process conditions and analytical results of the polythiol composition of Example 51. The analytical results were determined via gas chromatography. The following abbreviations and conventions are used in Table V: TEP=triethylphosphite; Phosphite Weight Percentage=(weight of phosphite compound/weight of cyclododecatriene)×100; $H_2S$ Molar Ratio=Moles of $H_2S$/moles of olefinic double bond of cyclododecatriene; AIBN Weight Percentage=(weight of AIBN/weight of cyclododecatriene)×100; CDDT=unreacted cyclododecatriene; monoS=total amount having one sulfur; diSH=dimercaptocyclododecene; SH-cyclicS=monothiol intramolecular sulfide compounds; diS total=total amount having two sulfurs; triSH=trimercaptocyclododecane; and sulfide dimer=thiol-containing intermolecular sulfide compounds.

Examples 52-58

Polythiol Compositions Produced from Trivinylcyclohexane, Before and after Wiped Film Evaporation Examples 52, 53, 55, and 57 were polythiol compositions produced generally in the manner described in Examples 34-44. Examples 52 and 53 were subjected to wiped film evaporation to produce Example 54, Example 55 was subjected to wiped film evaporation to produce Example 56, and Example 57 was subjected to wiped film evaporation to produce Example 58. These examples utilized the wiped film evaporation procedure described above. Table VI summarizes analytical results of the polythiol compositions of Examples 52-58. The abbreviations and conventions used in Table III also apply to Table VI.

As demonstrated in Table VI, the wiped film evaporation process significantly reduced phosphorus compounds, TVCH, monoSH, and diSH, and increased triSH and Heavies.

TABLE VI

Polythiol Compositions Derived from Trivinylcyclohexane, before and after wiped film evaporation - Examples 52-58.

| Example | 52 | 53 | 54 | 55 | 56 | 57 | 58 |
|---|---|---|---|---|---|---|---|
| Wt. % SH (titration) | 27.9 | 27.7 | 27.9 | 28.2 | 29.0 | 25.4 | 25.6 |

TABLE V

Thiolation of Cyclododecatriene in the presence of AIBN - Example 51.

| Example | Weight CDDT (g) | Weight $H_2S$ (g) | Phosphite Compound | Phosphite Weight Percentage | $H_2S$ Molar Ratio | AIBN Weight Percentage | Reaction Time (min) | % Conversion |
|---|---|---|---|---|---|---|---|---|
| 51 | 12 | 376 | TEP | 4.1 | 50 | 4.1 | 90 | 88 |

| Example | % CDDT | % monoS | % diSH | % SH-cyclicS | % diS total | % triSH | % sulfide dimmer | Ratio triSH/ diSH |
|---|---|---|---|---|---|---|---|---|
| 51 | 9.16 | 22.43 | 29.54 | 21.19 | 50.73 | 13.55 | 0.23 | 0.46 |

TABLE VI-continued

Polythiol Compositions Derived from Trivinylcyclohexane, before and after wiped film evaporation - Examples 52-58.

| Example | 52 | 53 | 54 | 55 | 56 | 57 | 58 |
|---|---|---|---|---|---|---|---|
| GC Analysis: | | | | | | | |
| TVCH | 1.89 | 1.31 | 0.00 | 1.46 | 0.00 | 0.43 | 0.00 |
| monoSH | 7.10 | 0.59 | 0.00 | 0.94 | 0.00 | 0.56 | 0.11 |
| diSH | 38.84 | 2.51 | 1.41 | 15.56 | 7.09 | 5.28 | 0.70 |
| cyclic sulfide | 3.09 | 5.32 | 1.46 | 4.60 | 3.97 | 5.77 | 0.78 |
| TriSH | 40.51 | 63.99 | 71.82 | 60.57 | 71.98 | 52.59 | 58.38 |
| Heavies (dimer) | 4.34 | 17.45 | 25.32 | 9.58 | 16.96 | 20.73 | 39.49 |
| Phosphorus Compounds | 4.15 | 8.60 | 0.00 | 7.09 | 0.00 | 12.04 | 0.05 |
| % Conversion | 79.1 | 96.5 | 97.7 | 91.7 | 96.3 | | |

Examples 59-64

Polythiol Compositions Produced from Cyclododecatriene, Before and after Wiped Film Evaporation Examples 61 and 63 were polythiol compositions produced generally in the manner described in Examples 1-23. Example 61 was subjected to wiped film evaporation to produce Example 62, and Example 63 was subjected to wiped film evaporation to produce Example 64. Examples 59 and 60 were produced from a composite of several polythiol compositions that were subjected to wiped film evaporation; no analysis of the composite was performed prior to wiped film evaporation. These examples utilized the wiped film evaporation procedure described above. Table VII summarizes analytical results of the polythiol compositions of Examples 59-64. The abbreviations and conventions used in Table I also apply to Table VII.

As demonstrated in Table VII, the wiped film evaporation process significantly reduced phosphorus compounds, CDDT, and mono S, and increased triSH.

TABLE VII

Polythiol Compositions Derived from Cyclododecatriene, before and after wiped film evaporation - Examples 59-64.

| Example | 59 | 60 | 61 | 62 | 63 | 64 |
|---|---|---|---|---|---|---|
| GC Analysis: | | | | | | |
| CDDT | 0.00 | 0.00 | 0.86 | 0.03 | 0.84 | 0.03 |
| mono S | 1.81 | 1.29 | 24.17 | 1.63 | 26.89 | 0.99 |
| di-SH | 43.81 | 39.89 | 36.62 | 40.46 | 32.28 | 12.50 |
| SH-cyclic S | 9.36 | 11.24 | 5.52 | 8.02 | 4.90 | 4.21 |
| tri-SH | 44.96 | 47.41 | 18.41 | 46.31 | 12.59 | 69.77 |
| Heavies (dimer) | 0.00 | 0.00 | 0.19 | 3.42 | 0.20 | 12.29 |
| Phosphorus Compounds | 0.00 | 0.00 | 13.61 | 0.10 | 21.86 | 0.10 |
| Ratios | | | | | | |
| triSH/diSH | 1.03 | 1.19 | 0.50 | 1.15 | 0.39 | 5.58 |
| triSH/SH-cyclic S | 4.80 | 4.22 | 3.34 | 5.77 | 2.56 | 14.24 |
| triSH/total diS | 0.85 | 0.93 | 0.44 | 0.96 | 0.34 | 1.88 |

We claim:

1. A polythiol composition comprising sulfur-containing compounds, wherein the sulfur-containing compounds of the polythiol composition comprise:
   from 30 to 85 wt. % tri(2-mercaptoethyl)cyclohexane; and
   from 0.1 to 60 wt. % di(2-mercaptoethyl)vinylcyclohexane.

2. The composition of claim 1, wherein the polythiol composition comprises less than 10 wt. % trivinylcyclohexane.

3. The composition of claim 2, wherein the sulfur-containing compounds of the polythiol composition comprise from 20 to 55 wt. % di(2-mercaptoethyl)vinylcyclohexane.

4. The composition of claim 1, wherein the sulfur-containing compounds of the polythiol composition comprise from 0.1 to 10 wt. % di(2-mercaptoethyl)vinylcyclohexane.

5. The composition of claim 1, wherein the sulfur-containing compounds of the polythiol composition comprise an average of from 0.3 to 6 wt. % sulfide sulfur.

6. The composition of claim 1, wherein the sulfur-containing compounds of the polythiol composition comprise less than or equal to 5 wt. % (2-mercapto-ethyl)divinylcyclohexane.

7. The composition of claim 1, wherein a weight ratio of tri(2-mercaptoethyl)cyclohexane to di(2-mercaptoethyl)vinylcyclohexane in the polythiol composition is in a range from 2:1 to 60:1.

8. The composition of claim 1, wherein a weight ratio of intermolecular sulfide compounds to intramolecular sulfide compounds in the polythiol composition is in a range from 1:1 to 30:1.

9. The composition of claim 1, wherein the sulfur-containing compounds of the polythiol composition comprise an average of from 22 to 34 wt. % thiol sulfur.

10. A process for forming the polythiol composition of claim 1, the process comprising:
   1) contacting
      a) trivinylcyclohexane;
      b) $H_2S$; and
      c) a phosphite compound; and
   2) forming the polythiol composition;
   wherein a molar ratio of $H_2S$ to olefinic double bonds of trivinylcyclohexane is in a range from 10:1 to 500:1.

11. The process of claim 10, wherein the phosphite compound comprises a compound having the formula:

$$P(OR^1)_3;$$

wherein each $R^1$ is independently a $C_1$-$C_{10}$ hydrocarbyl group.

12. The process of claim 10, wherein the phosphite compound comprises trimethylphosphite, triethylphosphite, tributylphosphite, or any combination thereof.

13. The process of claim 10, wherein:
   the molar ratio of $H_2S$ to olefinic double bonds of trivinylcyclohexane is in a range from 30:1 to 500:1; and
   a molar ratio of the phosphite compound to olefinic double bonds of trivinylcyclohexane is in a range from 0.003:1 to 0.10:1.

14. The process of claim 10, wherein:
   the molar ratio of $H_2S$ to olefinic double bonds of trivinylcyclohexane is in a range from 40:1 to 250:1; and
   a molar ratio of the phosphite compound to olefinic double bonds of trivinylcyclohexane is in a range from 0.006:1 to 0.05:1.

15. The process of claim 10, wherein the polythiol composition is formed in the presence of ultraviolet light.

16. The process of claim 10, wherein the polythiol composition is formed in the presence of ultraviolet light and a photoinitiator.

17. The process of claim 10, wherein the polythiol composition is formed at conditions suitable for a thermal decomposition of a free radical initiator.

18. The process of claim 10, wherein the polythiol composition is formed in the presence of a hydrocarbon solvent, an aromatic hydrocarbon solvent, a ketone solvent, an alcohol solvent, an ether solvent, or any combination thereof.

19. The process of claim 10, wherein at least 65% of the olefinic double bonds of trivinylcyclohexane have reacted to form a sulfur-containing group.

20. The process of claim 10, further comprising a step of separating at least a portion of the $H_2S$, of the phosphite compound, of trivinylcyclohexane, of compounds having only one sulfur atom, or combinations thereof.

21. The process of claim 20, wherein the $H_2S$, the phosphite compound, trivinylcyclohexane, the compounds having only one sulfur atom, or combinations thereof, are removed by wiped film evaporation, distillation, short path distillation, or a combination thereof.

* * * * *